US011266611B2

(12) United States Patent
Rubin

(10) Patent No.: US 11,266,611 B2
(45) Date of Patent: Mar. 8, 2022

(54) MORE POTENT AND LESS TOXIC FORMULATIONS OF EPINEPHRINE AND METHODS OF MEDICAL USE

(71) Applicant: Darren Rubin, Largo, FL (US)

(72) Inventor: Darren Rubin, Largo, FL (US)

(73) Assignee: ETON PHARMACEUTICALS, INC., Deer Park, IL (US)

( * ) Notice: Subject to any disclaimer, the term of this patent is extended or adjusted under 35 U.S.C. 154(b) by 0 days.

(21) Appl. No.: 15/991,501

(22) Filed: May 29, 2018

(65) Prior Publication Data

US 2018/0333374 A1 Nov. 22, 2018

Related U.S. Application Data

(63) Continuation-in-part of application No. 15/616,157, filed on Jun. 7, 2017, now Pat. No. 10,039,728, which is a continuation-in-part of application No. 15/596,440, filed on May 16, 2017, now Pat. No. 10,004,700.

(51) Int. Cl.
| | |
|---|---|
| *A61K 31/137* | (2006.01) |
| *A61K 47/26* | (2006.01) |
| *A61P 9/02* | (2006.01) |
| *A61P 41/00* | (2006.01) |
| *A61P 7/04* | (2006.01) |
| *A61K 47/02* | (2006.01) |
| *A61K 9/00* | (2006.01) |
| *A61K 45/06* | (2006.01) |

(52) U.S. Cl.
CPC ............ *A61K 31/137* (2013.01); *A61K 47/26* (2013.01); *A61P 7/04* (2018.01); *A61P 9/02* (2018.01); *A61P 41/00* (2018.01); *A61K 9/0019* (2013.01); *A61K 9/0085* (2013.01); *A61K 45/06* (2013.01); *A61K 47/02* (2013.01); *A61K 2300/00* (2013.01)

(58) Field of Classification Search
CPC ...... A61K 31/137; A61K 47/26; A61K 47/02; A61K 9/0019; A61K 45/06; A61K 2300/00; A61P 9/02; A61P 41/00; A61P 7/04

See application file for complete search history.

(56) References Cited

U.S. PATENT DOCUMENTS

| | | | |
|---|---|---|---|
| 5,002,973 | A | 3/1991 | Zeleznick et al. |
| 9,119,876 | B1 | 9/2015 | Kannan et al. |
| 9,283,197 | B1 | 3/2016 | Taneja |
| 9,295,657 | B1 | 3/2016 | Kannan et al. |
| 10,004,700 | B1 | 6/2018 | Taneja |
| 10,039,728 | B1 | 8/2018 | Taneja |
| 10,159,656 | B2 | 12/2018 | Rawas-Qalaji et al. |
| 2008/0269347 | A1 | 10/2008 | Bruss et al. |
| 2009/0318361 | A1 | 12/2009 | Noera et al. |
| 2012/0029085 | A1 | 2/2012 | Mackay |
| 2012/0322884 | A1 | 12/2012 | Rawas-Qalaji et al. |
| 2015/0246009 | A1 | 9/2015 | Gupta et al. |
| 2016/0045457 | A1 | 2/2016 | Rawas-Qalaji et al. |
| 2016/0374966 | A1 | 12/2016 | Rawas-Qalaji et al. |
| 2017/0071881 | A1 | 3/2017 | Rawas-Qalaji et al. |
| 2018/0147145 | A1 | 5/2018 | Rawas-Qalaji et al. |

FOREIGN PATENT DOCUMENTS

| | | |
|---|---|---|
| CA | 2002643 A1 | 5/1990 |
| WO | 2014057365 A1 | 4/2014 |

OTHER PUBLICATIONS

Schug SA, Saunders D, Kurowski I, Paech MJ. Neuraxial drug administration: a review of treatment options for anaesthesia and analgesia. CNS Drugs. 2006;20(11):917-33.*
American Regent, Inc., "Epinephrine—epinephrine injection, solution", May 13, 2011, 13 pages.
Connors, Kenneth A. et al., "Chemical Stability of Pharmaceuticals Handbook for Pharmacists—Section Re: Epinephrine", John Wiley & Sons; 2nd Edition, 1986, Second Edition (12 pages)., 1986, pp. 438-447.
Fyllingen, G et al., "Racemisation and Oxidation in Adrenaline Injections", Acta Pharm. Nord., 1990, vol. 2, No. 5, 1990, pp. 355-362.
JHP Pharmaceuticals, LLC, , "Prescribing Information for Adrenalin", revised Dec. 2012 (10 pages)., Dec. 2012, 10 pages.
Kerddonfak, Saowanee , "The Stability and Sterility of Epinephrine Prefilled Syringe", Asian Pacific Journal of Allergy and Immunology; vol. 28, 2010, pp. 53-57.
Stepensky, David et al., "Long-Term Stability Study of L-Adrenaline Injections: Kinetics of Sulfonation and Racemization Pathways of Drug Degradation", Journal of Pharmaceutical Sciences, vol. 93, No. 4, Apr. 2004, pp. 969-980.
U.S. Distrct Crt. for The, Disrtict of Delaware , "Declaration of Matthew Freimuth, Esq., in Support of Hospira's Motion for Monetary Sanctions for Violation of Rule 11", Case No. 1:17-cv-00775-LPS, Sep. 1, 2017, 146 pages.
U.S. Distrct Crt. for The, Disrtict of Delaware , "Declaration of Matthew Freimuth, Esq., in Support of Hospira's Motion for Partial Summary Judgment of Non-Infringement Under the Doctrine of Equivalents", Case 1:17-cv-00775-LPS, Jan. 5, 2018, 122 pages.
U.S. Distrct Crt. for The, Disrtict of Delaware , "Declaration of Matthew Freimuth, Esq., in Support of Hospira's Motion to Dismiss Belcher's Complaint Under Rule 12(b)(6)", Case No. 1:17-cv-00075-LPS, Sep. 1, 2017, 110 pages.
U.S. Distrct Crt. for The, Disrtict of Delaware , "Declaration of Rodolfo Pinal, Ph.D., in Support of Hospira's Opening Claim Construction Brief", Case No. 1:17-cv-00775-LPS, Feb. 2, 2018, 99 pages.
U.S. Distrct Crt. for The, Disrtict of Delaware , "Defendant Hospira, Inc.'s Opening Claim Construction Brief", Case No. 1:17-cv-00775-LPS, Feb. 2, 2018, 43 pages.

(Continued)

*Primary Examiner* — Sahar Javanmard
(74) *Attorney, Agent, or Firm* — Wood, Phillips, Katz, Clark & Mortimer

(57) ABSTRACT

The present invention provides pharmaceutical formulations of levorotatory-epinephrine, 1-epinephrine, more potent and less toxic than existing pharmaceutical formulations of epinephrine, along with methods of producing and using these pharmaceutical formulations of 1-epinephrine, including preventing and or treating hypotension and hemostasis under surgical anesthesia.

7 Claims, No Drawings

(56) References Cited

OTHER PUBLICATIONS

U.S. Distrct Crt. for The, Disrtict of Delaware, "Defendant Hospira, Inc.'s Responsive Claim Construction Brief", Case No. 1:17-cv-00775-LPS, Mar. 12, 2018, 105 pages.
U.S. Distrct Crt. for The, Disrtict of Delaware, "Joint Claim Construction Chart", Case No. 1:17-cv-00775-LPS, Jan. 19, 2018, 18 pages.
U.S. Distrct Crt. for The, Disrtict of Delaware, "Memorandum Opinion", Case No. 1:17-cv-00775-LPS, Sep. 28, 2018, 14 pages.
U.S. Distrct Crt. for The, Disrtict of Delaware, "Opening Brief in Support of Hospira's Motion to Dismiss Belcher's Complaint Under Rule 12(b)(6)", Case No. 1:17-cv-00075-LPS, Sep. 1, 2017, 18 pages.
U.S. Distrct Crt. for The, Disrtict of Delaware, "Opening Brief in Support of Hospira's Motion for Monetary Sanctions for Violation of Rule 11", Case No. 1:17-cv-00075-LPS, Sep. 1, 2017, 25 pages.
U.S. Distrct Crt. for The, Disrtict of Delaware, "Opening Brief in Support of Hospira's Motion for Partial Summary-Judgment of Non-lnfringement Under the Doctrine of Equivalents", Case No. 1:17-cv-00075-LPS, Jan. 5, 2018, 25 pages.
U.S. Distrct Crt. for The, Disrtict of Delaware, "Plaintiff Belcher Pharmaceutical LLC's, Claim Construction Answering Brief", Case No. 17-00775 (LPS), Mar. 2, 2018, 180 pages.
U.S. Distrct Crt. for The, Disrtict of Delaware, "Plaintiff *Belcher Pharmaceuticals, LLC*'s Answering Brief in Opposition of Defendant *Hospira, Inc.*'s Motion to Dismiss Under Rule 12(b)(6)", Case No. 17-00175 (LPS), Oct. 9, 2017, 17 pages.
U.S. Distrct Crt. for The, Disrtict of Delaware, "Plaintiff *Belcher Pharmaceuticals, LLC*'s Answering Brief in Opposition of Defendant *Hospira, Inc.*'s Motion to Monetary Sanctions for Violation of Rule 11", Case No. 17-00175 (LPS), Oct. 9, 2017, 21 pages.
U.S. Distrct Crt. for The, Disrtict of Delaware, "Reply Brief in Support of Hospira's Motion for Sanctions for Violation of Rule 11", Case 1:17-cv-00775-LPS, Oct. 23, 2017, 38 pages.
U.S. Distrct Crt. for The, Disrtict of Delaware, "Reply Brief in Support of Hospira's Motion for Summary Judgment of Non-lnfringement Under the Doctrine of Equivalents", Case No. 1:17-cv-00775-LPS, Mar. 12, 2018, 36 pages.
U.S. Distrct Crt. for The, Disrtict of Delaware, "Reply Brief in Support of Hospira's Motion to Dismiss Belcher's Complaint Under Rule 12(b)(6)", Case No. 1:17-cv-00775-LPS, Oct. 23, 2017, 19 pages.
U.S. District Crt. for The, District of Delaware, "Plaintiff Belcher Pharmaceutics, LLC, Initial Claim Construction Brief", Case No. 17-00775 (LPS), Feb. 2, 2018, 72 pages.
U.S. Distrct Crt. Middle, District of Florida Tampa Div., "Belcher Pharmaceuticals, LLC's Answer, Affirmative Defenses, and Counterclaims and Demand for Jury Trail", Case 8:18-cv-02379-WFJ-AAS, Nov. 7, 2018, 12 pages.
U.S. District Crt. Middle, District of Florida Tampa Div., "Complaint for Declaratory Judgment of Patent Non-lnfringement", Case 8:18-cv-02379-WFJ-AAS, Sep. 26, 2018, 39 pages.
Coralic, Zlatan, ""The Dirty Epi Drip: IV Epinephrine When You Need It"", Academic Life in Emergency Medicine (Jun. 27, 2013), url:https://www.aliem.com/2013/06/dirtyepi/.
Gherezghiher, Tseggai et al., "Ocular Effects of Adrenergic Stereoisomers in the Rabbit", Journal of Ocular Pharmacology; vol. 1 No. 1, 1985, pp. 19-28.
Innes, Ian R. et al., "The Pharmacological Basis of Therapeutics", Editors: Goodman & Gilman; 5th Edition; Chapter 24 Norepinephrine, Epinephrine, and the Sympathomimetic Amines, 1975, pp. 477 & 483.
International Medication Systems, "Epinephrine—epinephrine injection", May 2015, 8 pages.
Moed, H.D. et al., "Synthesis of B-Phenyl-Ethylamine Derivatives III Bronchodilators", Recueil; vol. 74, 1955, pp. 919-936.
Scholar Chemistry, "Material Safety Data Shee—Hydrochloric Acid Solutions, 0.5M", MSDS # 338.10, Feb. 2, 2009, 2 pages.
Scholar Chemisty, "Material Safety Data Sheet—Hydrochloric Acid Solution, 1.0M", MSDS # 338.00, Jan. 23, 2009, 2 pages.
Szulczewski, Dale H. et al., "Epinephrine", Analytical Profiles of Drugs Substances vol. 7, 1978, pp. 193-229.
U.S. Distrct Crt. for The, Disrtict of Delaware, "Defendant Hospira, Inc.'s Responsive Post-Trial Brief", Case No. 17-cv-775-LPS; Redacted-Pubilic Version, Aug. 9, 2019, 33 pages.
U.S. Distrct Crt. for The, Disrtict of Delaware, "Defendant Hospira, Inc.'s Opening Post-Trial Brief", Case No. 17-cv-775-LPS; Redacted-Public Version, Jul. 26, 2019, 37 pages.
U.S. Distrct Crt. for The, Disrtict of Delaware, "Plaintiff Belcher Pharmaceuticals, LLC's Post-Trial Answering Brief", Case No. 17-CV-775-LPS; Filed Under Seal, Aug. 9, 2019, 36 pages.
U.S. Distrct Crt. for The, Disrtict of Delaware, "Plaintiff Belcher Pharmaceuticals, LLC's Post-Trial Reply Brief", Case No. 17-CV-775-LPS, Aug. 23, 2019, 23 pages.
U.S. Pharmacopeia, , "Ephedrine", Official Monographs, 2009, pp. 2258-2266.
U.S. Pharmacopeia, "Epinephrine", Official Monographs, 2004, pp. 710-713.
U.S. Pharmacopeia, "Injections, Particulate Matter in Ophthalmic Solutions, Physical Tests, General Information, Official Monographs", Official Monographs; vol. 1 & 2; vol. 1—pp. 38, 402, 403, 1141,1167, 1181; vol. 2—pp. 2805-2811, 2014.
Vidal-Ollivier, E. et al., "Assay for epinephrine and its impurities using reversed-phase high-performance liquid chromatography", Journal of Chromatography vol. 396, 1987, pp. 421-424.
Chaubal, Mahesh V. et al., "Chapter 16—Excipient Selection and Criteria for Injectable Dosage Forms", Excipient Development for Pharmaceutical, Biotechnology, and Drug Delivery Systems, 2006, pp. 271-290.
Inotropes & Vasopressors, The Department of Anaesthesia & Intensive Care, Chinese University, Hong Kong (CUHK) Dec. 1999, obtained from https://www.aic.cuhk.edu.hk/web8/inotropes.htm on Nov. 1, 2019.
Graham, et al., "Critical care in the emergency department: shock and circulatory support" Emerg Med J 22:17-21, 2005.
"Adrenalin" Prescribing Information, 11 pages, revised Dec. 2013, JHP Pharmaceuticals, Rochester, MI.
"Adrenaline (Epinephrine) 1 in 1000 Solution for Injection BP" 24 pages, Medicines and Healthcare Products Regulatory Agency.
"Adrenaline (Epinephrine)" drug review, Nov. 29, 2012, JHP Pharmaceuticals LLC, FDA; Center for Drug Evaluation and Research.
"Critical Care Medication Manual; Department of Nursing and Pharmacy Guidelines for Use of Intravenous Epinephrine Constant Infusion" manual, 3 pages, Nov. 2002, Anne Arundel Medical Center.
"DOPRAM-doxapram hydrochloride injection" drug label, 10 pages, Baxter Healthcare Corporation, Deerfield, IL.
"Epinephrine Injection, USP auto-injector" prescribing information, Jan. 2010, Greenstone LLC, Peapack, NJ.
"Epinephrine" 58 pages, National Library of Medicine HSDB Database, Toxnet: Toxicology Data Network, retrieved on Nov. 5, 2012 from http://toxnet.nlm.nih.gov/cgi-bin/sis/search/a?dbs+hsdb:@term+@DOCNO+4289.
"Epinephrine" The Merck Index, Fourteenth Edition, Merck Sharp & Dohme Corp., Whitehouse Station, NJ.
"L(−)-Epinephrine", chemical properties, online entry, Chemical Book.
"Levophed; Norepinephrine Bitartrate Injection, USP" drug label, 5 pages, Nov. 2009, Hospira, Inc., Lake Forest, IL.
"Septic Shock: Improving Patient Outcomes".
Vasopressors for Septic Shock (from the Surviving Sepsis Guidelines), online article, posted Sep. 13, 2013, PulmCCM, retrieved from https://pulmccm.org/review-articles/vasopressors-septic-shock-surviving-sepsis-guidelines/.
Par Pharmaceutical, Inc., Prescribing Information for Adrenalin, revised Sep. 2016.
Project Team of the Resuscitation Council (UK), "Emergency Medical Treatment of Anaphylactic Reactions" consensus guidelines, vol. 41, pp. 93-99, 1999, Resuscitation: Elsevier.
"Isoproterenol—Brands, Medical Use, Clinical Data" drug information sheet, retrieved from druglib.com.

(56) References Cited

OTHER PUBLICATIONS

Abbo, et al. "Cardiopulmonary Resuscitation Outcomes in Hospitalized Community-Dwelling Individuals and Nursing Home Residents Based on Activities of Daily Living", The American Geriatrics Society, vol. 61, pp. 34-39, 2013.

Abboud, et al., "Pharmacokinetics of Epinephrine in Patients With Septic Shock: Modelization and Interaction with Endogenous Neurohormonal Status", Critical Care Journal, vol. 13, 8 pages, Jul. 21, 2009.

Aburawi, et al., "Persistent Wandering Atrial Pacemaker After Epinephrine Overdosing—A Case Report", BMC Pediatrics journal, vol. 13, Issue 1, 2013, 3 pages.

Allwood, et al., "Peripheral Vascular Effects of Noradrenaline, Isopropylnoradrenaline and Dopamine", British Medical Bulletin, vol. 19, Issue 2, pp. 132-136, 1963.

Angus, et al., "Epidemiology of Severe Sepsis in the United States Analysis of Incidence, Outcome, and Associated Costs of Care", Critical Care Medicine, vol. 269, No. 7, pp. 1303-1310, 2001.

Annane, et al., "Norepinephrine Plus Dobutamine Versus Epinephrine Alone for Management of Septic Shock: A Randomised Trial", The Lancet, vol. 370, pp. 676-684, Aug. 25, 2007.

Auleitta, "Effect of Epinephrine on Implantation and Foetal Survival in the Rabbit", Journal of Reproductive Fertility, vol. 27, pp. 281-282, Jun. 2, 1971.

Berben, et al., "Etiology and Prevention of Sloughs Produced by L-Norepinephrine", Annals of Surgery, vol. 146, No. 6, pp. 1016-1020, Dec. 1957.

Berk, et al. "Enhanced Glycemic Responsiveness to Epinephrine in Insulin-Dependent Diabetes Mellitus Is the Result of the Inability to Secrete Insuline", The American Society for Clinical Investigation, Inc, vol. 75, pp. 1842-1851, Jun. 1985.

Bollaert, et al., "Effects of Epinephrine on Hemodynamics and Oxygen Metabolism in Dopamine-Resistant Septic Shock", American College of Chest Physicians, vol. 98, No. 4, pp. 949-953, Oct. 1990.

Bone, et al. "Definitions for Sepsis and Organ Failure and Guidelines for the Use of Innovative Therapies in Sepsis", American College of Chest Physicians, vol. 101, No. 6, pp. 1644-1655, Jun. 1992.

Breil, et al., "Randomised Study of Hypertonic Saline Infusion During Resuscitation from Out-of-Hospital Cardiac Arrest", Resuscitation Journal, vol. 83, pp. 347-352, 2012, Elsevire Ireland Ltd.

Breuer, et al. "Pharmacokinetics and Pharmacodynamics of Moist Inhalation Epinephrine Using a Mobile Inhaler", European Journal of Clinical Pharmacology, vol. 69, pp. 1302-1310, Jan. 5, 2013.

Brierly, et al., "Distinct Hemodynamic Patterns of Septic Shock at Presentation to Pediatric Intensive Care", Pediatrics, vol. 122, No. 4 pp. 752-759, Oct. 2008.

Brierley, et al., "Clinical Practice Parameters for Hemodynamic Support of Pediatric and Neonatal Septic Shock: 2007 update from the American College of Critical Care Medicine", Society of Critical Care Medicine, vol. 37, No. 2, pp. 666-688, 2009.

Brock, et al., "Cardiac Sensitization: Methodology and Interpretation in Risk Assessment", Regulatory Toxicology and Pharmacology, vol. 38, pp. 78-90, 2003.

Brown "Therapeutic Controversies in the Management of Acute Anaphylaxis", Journal Accid. Emerg. Med, vol. 15, pp. 89-95, 1998.

Calzia, et al., "Epinephrine Kinetics in Septic Shock—A Means to Understand Variable Catecholamine Efficiency?", Critical Care, commentary, vol. 13, No. 4, 2 pages, Aug. 13, 2009.

Carr, "Stability of Epinephrine at Standard Concentrations", Can. J. Hosp. Pharm, vol. 67, No. 3, pp. 197-202, May 2014.

Carroll, et al., "Vasopressin Rescue for In-Pediatric Intensive Care Unit Cardiopulmonary Arrest Refractory to Initial Epinephrine Dosing: A Prospective Feasibility Pilot Trial", Pediatric Critical Care Medicine, vol. 13, No. 3, pp. 265-272.

Cassidy, et al., "Epinephrine: Systemic Effects And Varying Concentrations In Local Anesthesia", Anesthesia Progress, review, pp. 289-297, Nov. 1986.

Ceneviva, et al., "Hemodynamic Support in Fluid-Refractory Pediatric Septic Shock", Pediatrics, vol. 102, No. 2, 6 pages, Aug. 1998.

Chen, et al., "Pulmonary Edema and Hemorrhage as a Consequence of Systemic Vasoconstriction", American Journal of Physiology, vol. 227, No. 1, pp. 144-151, Jul. 1974.

Chilian, et al., "Effects of Epinephrine on Coronary Microvascular Diameters", Coronary Microvascular Constriction, vol. 61, No. 5, pp. 47-53 Nov. 1, 1987.

Close, et al., "Cutaneous Necrosis Due to Norepinephrine: II. Mechanism and Prevention", Annals of Surgery, investigation, vol. 147, No. 1, pp. 44-50, Jan. 1958.

Clutter, et al. "Epinephrine Plasma Metabolic Clearance Rates and Physiologic Thresholds for Metabolic and Hemodynamic Actions in Man", The American Society for Clinical Investigation, Inc., vol. 66, pp. 94-101, Jul. 1980.

Corbett, et al., "Intraocular Adrenaline Maintains Mydriasis During Cataract Surgery", British Journal of Ophthalmology, vol. 78, pp. 95-98, 1994.

Cryer, et al., "Epinephrine and Norepinephrine are Cleared Through Beta-Adrenergic, But Not Alpha-Adrenergic, Mechanisms in Man" Metabolism, vol. 29, No. 11, pp. 1114-1118, Nov. 1980.

Cunnington, et al., "Epinephrine-Induced Myocardial Infarction in Severe Anaphylaxis: Is Nonselective B-Blockade a Contributory Factor?" American Journal of Emergency Medicine, case report, vol. 31, pp. 759.e1-759.e2, 2013.

Da Silva, et al., "Nebulized 0.5, 2.5 and 5 ml L-epinephrine for PostExtubation Stridor in Children: A Prospective, Randomized, Double-Blind Clinical Trial", Intensive care Medicine, vol. 38, pp. 286-293, 2012.

Davidson, A.G. "A Spectropolarimetric Assay of (-)-Adrenaline In Compendial Formulations" Journal of Pharm. Pharmacol, Article, vol. 31, pp. 77-82, 1978.

Day, et al. "Effects of Dopamine and Epinephrine Infusions on Renal Hemodynamics in Severe Malaria and Severe Sepsis", Critical Care Medicine, abstract, vol. 28, No. 5, pp. 1353-1362, May 2000.

Day, et al., "The Effects of Dopamine and Adrenaline Infusions on Acid-Base Balance and Systemic Haemodynamics in Sever Infection" The Lancet, vol. 348, pp. 219-223, Jul. 27, 1996.

De Backer, et al., "Effects of Dopamine, Norepinephrine, and Epinephrine on the Splanchnic Circulation in Septic Shock: Which is Best?", Critical Care Medicine, vol. 31, No. 6, pp. 1659-1667.

De Oliveira, et al., "ACCM/PALS Haemodynamic Support Guidelines for Paediatric Septic Shock: An Outcomes Comparison With and Without Monitoring Central Venous Oxygen Saturation", Intensive Care Medicine, vol. 34, pp. 1065-1075, 2008.

Dellinger, et al., "Surviving Sepsis Campaign: International Guidelines for Management of Sever Sepsis and Septic Shock", Critical Care Medicine, vol. 36, No. 1, pp. 296-327, 2008.

Di Giantomasso, et al., "The Haemodynamic and Metabolic Effects of Epinephrine in Experimental Hyperdynamic Septic Shock", Intensive Care Medicine, vol. 31, pp. 454-462, 2005.

Doellman, et al., "Infiltration and extravasation; Update on Prevention and Management" The Art and Science of Infusion Nursing, vol. 32, No. 4, pp. 203-211, Jul./Aug. 2009.

Duarte, et al., "Mechanisms for Blood Pressure Lowering and Metabolic Effects of Thiazide and Thiazide-Like Diuretics", Expert Rev Cardiovasc Ther, vol. 8, No. 6, pp. 793-802, Jun. 2010.

Dünser, et al., "Arginine Vasopressin in Advanced Vasodilatory Shock: A Prospective, Randomized, Controlled Study", Circulation, vol. 107, pp. 2313-2319, May 5, 2003, American Heart Association.

Duranteau, et al., "Effects of Epinephrine, Norepinephrine, or the Combination of Norepinephrine and Dobutamine on Gastric Mucosa in Septic Shock", Critical Care Medicine, vol. 27. No. 5, pp. 893-900, May 1999, Lippincott Williams & Wilkins, Inc.

Edwards, et al., "Bioavailibility of Epinephrine from Auvi-Q Compared with EpiPen" American College of Allergy, Asthma & Immunology, vol. 111, pp. 132-137, 2013.

Eisenhofer, et al., "Catecholamine Metabolism: A Contemporary View with Implications for Physiology and Medicine", Pharmacological Reviews, vol. 56, No. 3, pp. 331-349, 2004.

(56) References Cited

OTHER PUBLICATIONS

Eisenhofer, et al., "Regional Release and Removal of Catecholamines and Extraneuronal Metabolism to Metanephrines", The Endocrine Society, vol. 80, No. 10, pp. 3009-3017, 1995.
Eisenhofer "The Role of Neuronal and Extraneuronal Plasma Membrane Transporters in the Inactivation of Peripheral Catecholamines", Pharmacology & Therapeutics, vol. 91, pp. 35-62, 2001.
Ellis, et al., "The Role of Epinephrine in the Treatment of Anaphylaxis", Current Science Inc., vol. 3, pp. 11-14, 2003.
El-Shanawany, et al., "Clinical Immunology Review Series: An Approach to the Patient with Anaphylaxis", Clinical and Experimental Immunology, vol. 153, pp. 1-9, 2008.
Ensinger, et al., "Relationship Between Arterial and Peripheral Venous Catecholamine Plasma Catecholamine Concentrations During Infusion of Noradrenaline and Adrenaline in Healthy Volunteers" European Journal Clinical Phar, vol. 43, pp. 245-249, 1995.
Erdelyi, et al., "Urine Catecholamine in Paediatrics", Arch Did Child Educ Pract Ed, vol. 95, pp. 107-111, 2011.
Fisher, et al., "Pharmacokinetics of Exogenous Epinephrine in Critically Ill Children", Critical Care Medicine, vol. 21, No. 1, pp. 111-117, Jan. 1993.
Fisher "Treatment of Acute Anaphylaxis", British Medical Journal, vol. 311, No. 7007, pp. 731-733, Sep. 16, 1995.
Fitch, et al., "Optimal Management of Septic Shock", Postgraduate Medicine, vol. 111, No. 3, pp. 53-66, Mar. 2002.
Floras, et al., "Desipramine Blocks Augmented Neurogenic Vasoconstrictor Responses to Epinephrine", Hypertension, vol. 15, pp. 132-139, 1990, American Heart Association.
Funkenstein, et al., "Psychophysiological Study of Mentally Ill Patients", American Journal of Psychiatry, vol. 106, No. 1, pp. 16-29, Jul. 1949.
Gaffney, et al., "Effects of Reserpine and Guanethidine on Venous Reflexes" Circulation Research, vol. 11, pp. 889-894, Nov. 1962.
Gaffney, et al., "Study of the Relationship Between the Neurotransmitter Store and Adrenergic Nerve Block Induced by Reserpine and Guanethidine", Circulation Research, vol. 12, pp. 264-268, Mar. 1963.
Gei, et al., "The Use of a Continuous Infusion of Epinephrine for Anaphylactic Shock During Labor", The American College of Obstetricians and Gynecologists, case report, vol. 102, No. 6, pp. 1332-1335, Dec. 2003.
Glick, et al., "Mechanisms of Reflex Vasodilation: Assessment of the role of Neural Reuptake of Norepinephrine and Release of Histamine", The Journal of Clinical Investigation, vol. 447, pp. 511-520, 1968.
Glover, et al., "Wide Variability in Drug Use in Out-of-Hospital Cardiac Arrest: A Report from the Resuscitation Outcomes Consortium" Resuscitation, vol. 83, pp. 1324-1330, 2012, Elsevier.
Goldstein "Catecholamines 101", vol. 20, No. 6, pp. 331-352, Dec. 2010, Clin Auton Res.
Gomez-Moreno, et al., "Pharmacological Interactions of Vasoconstrictors", Med Oral Patol Oral Cir Bucal, review, Vo. 14, No. 1, pp. E20-E27, Jan. 1, 2009.
Goodman, et al., "The Pharmacological Basis of Therapeutics Adrenergic Agonists and Antagonists", 12th edition, Section 11, Chapter 12, The McGraw-Hill Companies.
Gordon, et al., "Blood Pressure Changes in Normals and in Hypertensives After Intravenous Epinephrine and Histamine" The Journal of Clinical Investigation, vol. 14, No. 3 ,pp. 367-372, 1935.
Gore, et al., "Lactic Acidosis During Sepsis Is Related to Increased Pyruvate Production, Not Deficits in Tissue Oxygen Availability" Annals of Surgery, Vo. 224, No. 1, pp. 97-102, 1996, Lippincott-Raven Publishers.
Grant, et al., "Environmental Temperature Variations Cause Degradations in Epinephrine Concentration and Biological Activity", American Journal of Emergency Medicine, vol. 12, No. 3, pp. 319-322, May 1994.
Green, et al., "A Polymorphism of the Human B2-Adrenergic Receptor Within the Fourth Transmembrane Domain Alters Ligand Binding and Functional Properties of the Receptor" The J. of Biological Chemistry, vol. 268, No. 31, pp. 23116-23121, Nov. 5, 1993.
Grob, et al., "Management of Mydrasis and Pain in Cataract and Intraocular Lens Surgery: Review of Current Medication and Future Directions" Clinical Ophthalmology, vol. 8, pp. 1281-1289, 2014, Dove Press Journal.
Groeneveld, "Hypovolemic Shock" Critical Care Medicine; Principles of Diagnosis and Management in the Adult, Part II, Chapter 27, pp. 485-499, Dec. 4, 2007, 3rd Edition, Mosby.
Guillemin, et al., "Determination of Catecholamines in Plasma by High-Performance Liquid Chromatography", Clinical Chemistry, vol. 34, No. 9, pp. 1913-1914, 1988.
Haffner, et al., "Metabolic Effects of B2-Agonists", Journal of Clinical Pharmacy and Therapeutics, vol. 17, pp. 155-164.
Haider, et al., "Ischemic Heart Failure: Sustained Inotropic Response to Small Doses of I-Epinephrine Without Toxicity", The American Journal of Cardiology, vol. 35, pp. 504-513, Apr. 1975.
Haigh, et al., "A Relationship Between Adrenaline and the Mode of Action of Oxytocin and Oestrogen on Vascular Smooth Muscle", Journal Physiol. Great Britain, vol. 178, pp. 563-576, 1965.
Hall, et al., "Intravenous Epinephrine Abuse", The American Journal of Emergency Medicine, case report, vol. 5, No. 1, pp. 64-65, Jan. 1987, Elsevier.
Han, et al., "Early Reversal of Pediatric-Neonatal Septic Shock by Community Physicians Is Associated With Improved Outcome", Pediatrics, vol. 112, No. 4, pp. 793-799, Oct. 4, 2003.
Hansen, et al., "Effects of Carvedilol on the Metabolic, Hemodynamic, and Electrocardiographic Responses to Increased Plasma Epinephrine in Normal Subjects", Journal of Cardiovascular Pharmacology, vol. 27, pp. 853-859, 1994, Raven Press.
Hashimoto, "Arrhythmia Models for Drug Research: Classification of Antiarrhythmic Drugs", Journal of Pharmacological Sciences, vol. 103, pp. 333-346, 2007, The Japanese Pharmacological Society.
Havel, et al., "Vasopressors for Hypotensive Shock", The Cochrane Collaboration, review, 78 pages, Issue 5, John Wiley & Sons, Ltd.
Heckmann, et al., "Epinephrine Treatment of Hypotension in Very Low Birthweight Infants", Acta Paediatrica, vol. 91, No. 5, pp. 566-570, 2002, Taylor & Francis.
Herlitz, et al., "Adrenaline in Out-of Hospital Ventricular Fibrillation. Does it make any difference?", Resuscitation, vol. 29, pp. 195-201, 1995.
Higuchi, et al. "Kinetics and Mechanism of Formation of Dulfonate from Epinephrine and Bisulfite" Journal of the American Chemical Society, article, vol. 82 Issue 8, pp. 1904-1907, Apr. 20, 1960.
Hoellein, et al., "Ficts and Facts of Epinephrine and Norepinephrine Stability in Injectable Solutions", International Journal of Pharmaceutics, vol. 434, pp. 468-480, 2012, Elsevier B.V.
Hollenberg, "Vasopressor Support in Septic Shock", CHEST;review, vol. 132, pp. 1678-1687, 2007, American College of Chest Physicians.
Hughes, et al., "The QseC Adrenergic Signaling Cascade in Enterohemorrhagic E. coli (EHEC)", PLoS Pathogens, vol. 5, No. 8, 13 p. 2009.
Hull, et al., "Effect of Epinephrine on the Corneal Endothelium", American Journal of Ophthalmology, vol. 79, No. 2, pp. 245-250, Feb. 1975.
Hull, Effects of Epinephrine, Benzalkonium Chloride, and Intraocular Miotics on Corneal Endothelium, Southern Medical Journal, vol. 72, No. 11, pp. 1380-1381, Nov. 1978.
Humphreys, et al., "Skin Necrosis Following Intravenous Noradrenaline", British Medical Journal, vol. 2 pp. 1250-1252, Nov. 19, 1955.
Hussain, et al., "Vasopressin for the Management of Catecholamine-Resistant Anaphylactic Shock", Singapore Medical Journal; case report, vol. 49, No. 9, pp. e225-e228, 2008.
Ichinohe, et al., "The Influence of Propranolol on the cardiovascular Effects and Plasma Clearance of Epinephrine", American Dental Society of Anesthesiology, vol. 38, pp. 217-220, 1991.
Illi, et al., "The Effect of Entacapone on the Disposition and Hemodynamic Effects of Intravenous Isoproterenol and Epinephrine", Clinical Pharmacology & Therapeutics, vol. 58, No. 2, pp. 221-227, 1995, Mosby-Year Book, Inc.

(56) References Cited

OTHER PUBLICATIONS

Jain, "Multi-Organ Autonomic Dysfunction in Parkinson Disease", author manuscript, vol. 17, No. 2, pp. 77-83, Feb. 2011, Parkinsonism Related Disorder; NIH Public Access.

James, et al., "Lactate is an Unreliable Indicator of Tissue Hypoxia in Injury or Sepsis", The Lancet; hypothesis, vol. 354, pp. 505-508, Aug. 7, 1999.

Jern, et al., "Infusion of Epinephrine Augments Pressor Responses to Mental Stress", Hypertension, vol. 18, pp. 467-474, 1911, American Heart Association.

Judson, et al., "The Comparative Effects of Small Intravenous Doses of Epinephrine Upon Arterial Pressure and Pulse Rate in Normotensive Subjects and in Hypertensive Patients Before and After Thoracolumbar Sympathectomy", The Journal of Clinical Investigation, vol. 29, No. 10, pp. 1405-1413, 1950.

Kajander, et al., "Iatrogenic Inverted Takotsubo Syndrome Following Intravenous Adrenaline Injections for an Allergic Reaction", Journal of Cardiology, vol. 165, pp. e3-e5, 2013, Elsevier.

Kaji, et al., "Predictors of Neurologic Outcome in Patients Resuscitated from Out-of-Hospital Cardiac Arrest Using Classification and Regression Tree Analysis" The Journal of Emergency Medicine, vol. 48, No. 2, Feb. 1, 2015, pp. 1024-1028.

Katz, et al., "The Interaction of Anesthetic Agents and Adrenergic Drugs to Produce Cardiac Arrhythmias", Anesthesiology, pp. 763-784, Jul./Aug. 1968.

Khoueiry, et al., "Reverse Takotsubo Cardiomyopathy in the Setting of Anaphylaxis Treated with High-Dose Intravenous Epinephrine" The Journal of Emergency Medicine, vol. 44, No. 1, pp. 96-99, 2013, Elsevier Inc.

Kim, et al., "Gastric Ischemia After Epinephrine Injection in a Patient with Liver Cirrhosis", World Journal of Gastroenterology, vol. 19, No. 3, pp. 411-414, Jan. 21, 2013, Baishideng.

Koch, et al., "Serum Resistin Levels in Critically Ill Patients are Associated With Inflammation, Organ Dysfunction and Metabolism and May Predict Survival of Non-Septic Patients" Critical Care, vol. 13, No. 3, 9 pages, Jun. 19, 2009.

Koch-Weser, Jan, "Fundamentals of Clinical Cardiology", Koch-Weser "Fundamentals of Clinical Cardiology" American Heart Journal, vol. 90, No. 1, pp. 93-116, Jul. 1975.

Kukreja, et al., "Catecholamine-Induced Aggravation of Aortic and Coronary Atherosclerosis in Monkeys", Atherosclerosis, vol. 40, pp. 291-298, 1981, Elsevier/North-Holland Scientific Publishers, Ltd.

Kuller, et al., "Unexpected Effects of Treating Hypertension in Men with Electrocardiographic Abnormalities: A Critical Analysis", Circulation, vol. 73, No. 1, pp. 114-123, 1986, American Heart Association.

Landgarten, et al., "Cardiovascular Dysfunction in Sepsis and Septic Shock", Current Science Inc., vol. 2, pp. 251-459, 2000.

Larsen, et al., "Paradoxical Reflex Bradycardia After Epinephrine Infusion for Arrhythmia Induction in the Electrophysiology Laboratory" Heart Rhythm Society, vol. 4, No. 10, pp. 455-458, Oct. 2018, Elsevier.

Lartey, et al., "A Sudden Loss of Vision After Routine Cataract Surgery", Ghana Medical Journal, vol. 47, No. 2, pp. 96-99, Jun. 2013.

Le Tulzo, et al., "Effects of Epinephrine on Right Ventricular Function in Patients with Severe Septic Shock and Right Ventricular Failure: a Preliminary Descriptive Study", Intensive Care Medicine, vol. 23, pp. 664-670, 1997, Springer-Verlag.

Lee, et al., "Epinephrine Reaction Treated With Nitroglycerin", JAMA; letter to the editor, vol. 2020, No. 4, p. 219, Oct. 23, 1967.

Levy, et al., "Comparison of Norepinephrine and Dobutamine to Epinephrine for Hemodynamics, Lactate Metabolism, and Gastric Tonometric Variables in Septic Shock: a Prospective, Randomized Study" Intensive Care Medicine, vol. 23, pp. 282-287, 1997.

Levy, "Bench-to-Bedside Review: Is There A Place for Epinephrine in Septic Shock?" BioMed Central Ltd, vol. 9, pp. 561-565, 2005.

Levy, et al., "Cardiovascular Response to Dopamine and Early Prediction of Outcome in Septic Shock: A Prospective Multiple-Center Study", Critical Care Medicine, vol. 33, No. 10, pp. 2172-2177, Lippincott Williams & Wilkins.

Levy, et al., "Increased Muscle-to-Serum Lactate Gradient Predicts Progression Towards Septic Shock in Septic Patients", Intensive Care Medicine, vol. 36, pp. 1703-1709, 2010, Springer and ESICM.

Levy, et al., "Relation Between Muscle Na K ATPase Activity and Raised Lactate Concentrations in Septic Shock: A Prospective Study" The Lancet, vol. 365, pp. 871-875, Mar. 5, 2005.

Levy, et al., "2001 SCCM/ESICM/ACCP/ATS/SIS International Sepsis Definitions Conference", Intensive Care Medicine, vol. 29, pp. 530-538, 2003.

Lewis, et al., "Topical Therapies for Glaucoma: What Family Physicians Need to Know", American Family Physician, vol. 59, No. 7, pp. 1871-1879, Apr. 1, 1999.

Liang, et al., "Re-Investigation of the Effect of Adrenaline and Noradrenaline on Renal Function in Situ", Journal of Physiology, vol. 220, pp. 19-32, 1972, Great Britain.

Lillehei, et al., "The Nature of Irreversible Shock: Experimental and Clinical Observations", Annals of Surgery, vol. 160, No. 4, pp. 682-708, Oct. 1964.

Lindner, et al., "Randomised Comparison of Epinephrine and Vasopressin in Patients with Out-of-Hospital Ventricular Fibrillation", The Lancet, vol. 349, pp. 535-537, Feb. 22, 1997.

Liou, et al., "Effects of Intraocular Epinephrine on the Corneal Endothelium of Rabbits" Journal of Ocular Pharmacology and Therapeutics, vol. 18, No. 5, pp. 469-473, 2002, Mary Ann Liebert, Inc.

Liou, et al., "The Effect of Intracameral Adrenaline Infusion on Pupil Size, Pulse Rate, and Blood Pressure During Phacoemulsification", Journal of Ocular Pharmacology and Therapeutics, vol. 14, No. 4, pp. 357-361, 1998.

Lipman, et al., "Vasoconstrictor Effects of Adrenaline in Human Septic Shock", Anaesthesia and Intensive Care, vol. 19, No. 1, Feb. 1991.

Little "Thyroid Disorders. Part I: Hyperthyroidism" OOOOE, vol. 101, No. 3, pp. 276-284, Mar. 2006, Elsevier Inc.

Lloyd, et al., "The Effect of Oxytocin and Adrenaline on Blood Flow in the Hind Limb of the Dog Following Chronic Lumbar Sympathectomy" Journal of Physiology, vol. 198, pp. 43-52, 1967, Great Britain.

Lluch, et al., "Evidence for the Direct Effect of Adrenergic Drugs on the Cerebral Vascular Bed of the Unanesthetized Goat", Stroke, vol. 4, pp. 50-56, 1973, American Heart Association, Inc.

Lowe, et al., "Demonstration of Alpha and Beta Adrenergic Receptors in Canine Cerebral Vasculature" Stroke, vol. 2, pp. 193-200, 1971, American Heart Association.

Macarthur, et al., "Inactivation of Catecholamines by Superoxide Gives New Insights on the Pathogenesis of Septic Shock" PNAS, vol. 97, No. 17, pp. 9753-9758, Aug. 15, 2000.

Mackenzie, et al., "Adrenaline in Treatment of Septic Shock: Effects on Haemodynamics and Oxygen Transport" Intensive Care Medicine, vol. 17, pp. 36-39, 1997, Springer-Verlag.

Mackie, et al., "Epinephrine-Containing Test Dose During Beta-Blockade" Journal of Clinical Monitoring, vol. 7, pp. 213-216, 1991, Little, Brown and Company.

McVeigh, et al., "Endovascular Aneurysm Repair for Multiple Aneurysms as a Sequel of Hypereosinophilic Syndrome" Vascular and Endovascular Surgery, case report, vol. 48, No. 3, pp. 277-280, 2014, SAGE.

Mentzelopoulos, et al., "Vasopressin, Steroids, and Epinephrine and Neurologically Favorable Survival After In-Hospital Cardiac Arrest" JAMA, vol. 310, No. 3, pp. 270-279, Jul. 17, 2013.

Merck, "Adverse Effects of Epinephrine When Given to Patients Taking Propranolol (Inderal)" Emergency Nurses Association, vol. 21, No. 1, pp. 27-32, Feb. 1995.

Mezzacappa, et al., "The Effects of Epinephrine Administration on Impendance Cardiographic Measures of Cardiovascular Function" International Journal of Psychophysiology, vol. 31, pp. 189-196, 1999, Elsevier.

Miller, et al., "Exercise-Induced Anaphylaxis: A Serious But Preventable Disorder" Phys Sportsmed, abstract, vol. 36, No. 1, Dec. 2008.

(56) References Cited

OTHER PUBLICATIONS

Minneci, et al., "Differing Effects of Epinephrine, Norepinephrine, and Vasopressin on Survival in a Canine Model of Septic Shock" Am J Physiol Heart Circ Physiol, vol. 24, No. 5, pp. H2545-H2554, Aug. 19, 2004.

Moran, et al., "Epinephrine as an Inotropic Agent in Septic Shock: A Dose-Profile Analysis" Critical Care Medicine, vol. 21, No. 1, pp. 70-77, Jan. 1993, Williams & Wilkins.

Mustafa, et al., "A Comprehensive Review of Hypertension in Pregnancy" Journal of Pregnancy, vol. 2012, 19 pages, 2012.

Myburgh, et al., "A Comparison of Epinephrine and Norepinephrine in Critically Ill Patients" Intensive Care Medicine, vol. 34, pp. 2226-2234, 2008, Springer-Verlag.

Myburgh, "An Appraisal of Selection and use of Catecholamines in Septic Shock—Old Becomes New Again" Critical Care and Resuscitation, review, vol. 8, No. 4, pp. 353-360, Dec. 2006.

Napoli, et al., "Acute Effects of Triiodothyronine on Endothelial Function in Human Subjects" The Endocrine Society, vol. 92, No. 1, pp. 250-254, 2007.

Nino, et al., "Drug-Induced Left Ventricular Failure in Patients with Pulmonary Disease" CHEST, vol. 92, No. 4, pp. 732-736, Oct. 1987.

Njoroge, et al., "Enterohemorrhagic *Escherichia coli* Virulence Regulation by Two Bacterial Adrenergic Kinases, QseC and QseE" Infection and Immunity, vol. 80, No. 2, pp. 688-703, 2012, American Society for Microbiology.

Nordseth, et al., "Dynamic Effects of Adrenaline (Epinephrine) in Out-of-Hospital Cardiac Arrest With Initial Pulseless Electrical Activity" vol. 83, pp. 946-952, 2012, Resuscitation: Elsevier.

Novey, et al., "Alarming Reaction After Intravenous Administration of 30 ml of Epinephrine" JAMA, vol. 207, No. 13, pp. 2435-2436, Mar. 31, 1969.

Olasveengen, et al., "Outcome When Adrenaline (Epinephrine) was Actually Given vs. Not Given—post hoc Analysis of a Randomized Clinical Trial" Resuscitation, vol. 83, pp. 327-332, 2011, Elsevier.

Ong, et al., "A Randomised, Double-Blind, Multi-Centre Trial Comparing Vasopressin and Adrenaline in Patients with Cardiac Arrest Presenting to or in the Emergency Department" Resuscitation, vol. 83, pp. 953-960, 2012, Elsevier.

Palmer, et al., "Inotropes" Anaesthesia and Intensive Care Medicine, vol. 10, No. 8, pp. 362-366, Elsevier.

Paradis, et al., "Coronary Perfusion Pressure and the Return of Spontaneous Circulation in Human Cardiopulmonary Resuscitation" JAMA, vol. 263, pp. 1106-1113, Feb. 23, 1990.

Patel, et al., "Choice of Vasopressor in Septic Shock: Does it Matter?" Critical Care, vol. 11, No. 6, 2 pages, 2007, BioMed Central Ltd.

Patel, et al., "Epinephrine Induced Digital Ischemia After Accidental Injection from an Auto-Injector Device" Indian Pediatrics, correspondence, vol. 50, p. 247, 2013.

Peyko, et al., "Evaluation and Treatment of Accidental Autoinjection of Epinephrine" American Journal of Health-System Pharmacy, case reports, vol. 70, pp. 778-781, May 1, 2013.

Phillips, et al., "Hypertensive Emergencies: Diagnosis and Management" Progress in Cardiovascular Diseases, vol. 45, No. 1, pp. 33-48, Jul./Aug. 2002.

Pinto, et al., "Decrease in Repetitive Extrasystole Threshold During Epinephrine Infusion is Enhanced in Conscious Dogs With Perinephritic Hypertension" Physiology & Behavior, vol. 49, pp. 383-386, 1991, Pergamon Press.

Pong, et al., "Toxic Endothelial Cell Destruction Syndrome After Intraocular Lens Repositioning with Intracameral Epinephrine" Journal Cataract Refract Surgery, case report, vol. 34, pp. 1990-1991, 2008, ASCRS and ESCRS.

Portmann, et al. "Reaction Kinetics of Some Catecholamines in Sodium Bisulfite Solutions", Drug Development and Industrial Pharmacy, vol. 4, Issue 1, pp. 31-52, 1978.

Redding, et al., "Evaluation of Drugs for Cardiac Resuscitation", Anesthesiology, vol. 24, pp. 203-207, Mar. 1963.

Rivers, et al., "Early Goal-Directed Therapy in the Treatment of Severe Sepsis and Septic Shock" New England Journal of Medicine, vol. 345, No. 19, pp. 1368-1377, Nov. 8, 2001.

Robinson, et al., "The Effect of Norepinephrine Versus Epinephrine on Myocardial Hemodynamics During CPR" Annals of Emergency Medicine, vol. 18, pp. 336-340, Apr. 4, 1989.

Sadleir, et al., "Epinephrine (Adrenaline) Preventing Recovery From Intraoperative Anaphylactic Shock Complicated by Systolic Anterior Motion of the Mitral Valve with Left Ventricular Outflow Tract Obstruction on Transoesophageal Echocardiography", Anesthesia Intensive Care, Case Report, vol. 46, No. 6, pp. 566-571, 2018.

Sair, et al., "Tissue Oxygenation and Perfusion in Patients with Systemic Sepsis" Critical Care Medicine, vol. 29, No. 7, pp. 1343-1349, 2001.

Schummer, et al., "Extravasation Injury in the Perioperative Setting" Anesthesia & Analgesia, case report, vol. 100, pp. 722-727, 2005, International Anesthesia Research Society.

Seguin, et al., "Dopexamine and Norepinephrine Versus Epinephrine on Gastric Perfusion in Patients with Septic Shock: A Randomized Study" Critical Care, vol. 10, No. 1, 8 pages, 2006, BioMed Central Ltd.

Seguin, et al., "Effects of Epinephrine Compared with the Combination of Dobutamine and Norepinephrine on Gastric Perfusion in Septic Shock" American Society for Clinical Pharmacology and Therapeutics, vol. 71, No. 5, pp. 381-388, May 2002.

Shapiro, et al., "Skin Necrosis Following Intravenous Use of Norepinephrine" American Journal of Surgery, vol. 92, pp. 566-570, Oct. 1956.

Shaver, et al., "Acute Myocardial Infarction After Administration of Low-Dose Intravenous Epinephrine for Anaphylaxis" Canadian Journal of Emergency Medicine, case report, vol. 8, No. 4, pp. 289-294, Jul. 2006.

Sheikh, et al., "Adrenaline (Epinephrine) for the Treatment of Anaphylaxis with and Without Shock" The Cochrane Collaboration, Yeview, Issue 2, 18 pages, 2011 John Wiley & Sons, Ltd.

Shoroghi, et al., "Effect of Different Epinephrine Concentrations on Local Bleeding and Hemodynamics During Dermatologic Surgery" ACTA Dermatovenerologica Croatica, vol. 16, No. 4, pp. 209-214, 2008.

Simons, "Anaphylaxis" American Academy of Allergy, Asthma & Immunology, vol. 125, No. 2, pp. S161-S181, Feb. 2010.

Simons, "First-aid Treatment of Anaphylaxis to Food: Focus on Epinephrine" American Academy of Allergy, Asthma and Immunology, vol. 113, No. 5, pp. 837-844, May 2004.

Slack, et al., "A Bisulfite-Free Intraocular Epinephrine Solution" American Journal of Ophthalmology, vol. 110, pp. 77-82, Jul. 1990.

Slim, et al., "Older Blood Pressure Medications—Do They Still Have a Place?" The American Journal of Cardiology, vol. 108, pp. 308-316, 2011, Elsevier Inc.

Small, et al., "Pharmacology and Physiology of Human Adrenergic Receptor Polymorphisms" Annual Review of Pharmacology and Toxicology, vol. 43, pp. 381-411, 2003.

Smith, et al., "Protection of Transplantable Kidneys by Alpha Adrenergic Blockage" Annals of Surgery, vol. 173, No. 2, pp. 225-229, Feb. 1971.

Soar, et al., "Adrenaline-Proven Benefit in Cardiac Arrest at Last?", Resuscitation, editorial, vol. 82, pp. 1115-1116, 2011.

Stein, et al., "Basal and Stimulated Sympathetic Responses After Epinephrine: No Evidence of Augmented Responses" Hypertension, vol. 32, pp. 1016-1021, 1998, American Heart Association.

Stiell, et al., "Vasopressin Versus Epinephrine for Inhospital Cardiac Arrest: A Randomised Controlled Trial" The Lancet, vol. 358, pp. 105-109, Jul. 2001.

Stratton, et al., "Hemodynamic Effects of Epinephrine Concentration-Effect Study in Humans" Journal of Applied Physiology, vol. 58, No. 4, pp. 1199-1206, Apr. 1985, American Physiological Society.

"Effect of Intravenous Adrenaline on Electrocardiogram, Blood Pressure, and Serum Potassium" British Heart Journal, vol. 49, pp. 90-93, 1983.

Tanaka, et al., "T-Wave Amplitude as an Indicator for Detecting Intravascular Injection of Epinephrine Test Dose in Awake and

(56) References Cited

OTHER PUBLICATIONS

Anesthetized Elderly Patients" International Anesthesia Research Society, vol. 93, pp. 1332-1337, 2001.
Tang, et al., "The Effects of Biphasic and Conventional Monophasic Defibrillation on Postresuscitation Myocardial Function" Journal of the American College of Cardiology, vol. 34, No. 3, pp. 815-822, Sep. 1999, Elsevier.
Taylor, et al., "Interactions Between Corticosteroids and B Agonists" Thorax, vol. 55, pp. 595-602, 2000.
Totaro, et al., "Epinephrine-Induced Lactic Acidosis Following Cardiopulmonary Bypass" Critical Care Medicine, vol. 25, No. 10, pp. 1693-1699, Oct. 1997.
Trzeciak, et al., "Septic Shock" Critical Care Cardiovascular Disease, Part II, Chapter 24, pp. 439-452.
Tulen, et al., "Psychological, Cardiovascular, and Endocrine Changes During 6 Hours of Continuous Infusion of Epinephrine or Norepinephrine in Healthy Volunteers" Psychosomatic Medicine, vol. 55, pp. 61-69, 1993, The American Psychosomatic Society.
Tummala et al., "Cardiac Anaphylaxis: A Case of Acute ST-Segment Elevation Myocardial Infarction After IM Epinephrine for Anaphylactic Shock" The American Journal of Emergency Medicine, vol. 31, pp. 1157.e1-1157.e3, 2013; Elsevier.
Van Der Poll, et al., "Epinephrine Exerts Anticoagulant Effects During Human Endotoxemia" J. Exp. Med., vol. 185, No. 6, pp. 1143-1148, Mar. 17, 1997, The Rockefeller University Press.
Van Der Poll, et al., "Epinephrine Inhibits Endotoxin-Induced IL-1 B Production: Roles of Tumor Necrosis Factor-a and IL-10" The American Physiological Society, vol. 273, pp. R1885-R1890, 1997.
Van Prohaska, et al., "Epinephrine Hypertension; the Effect of the Continuous Intravenous Injection of Epinephrine on the Blood Pressure", Annals of Surgery, vol. 106, No. 5, pp. 857-867, Nov. 1937.
Vandycke, et al., "High Dose Versus Standard Dose Epinephrine in Cardiac Arrest—A Meta-Analysis", Resuscitation, vol. 45, pp. 161-166, 2000, Elsevier Sciences Ireland Ltd.
Vasudevan, et al., "Vasopressin Infusion in Children With Catecholamine-Resistant Septic Shock" ACTA Paediatrica, vol. 94, No. 3, pp. 380-383, 2005, Taylor & Francis Ltd.
Vlastarakos, et al., "Treating Common Problems of the Nose and Throat in Pregnancy: What is Safe?" Eur. Arch. Otorhinolaryngol, vol. 265, pp. 499-508, 2008, Springer-Verlag.
Walters, et al., "The Effect of Epinephrine on Glucose-Mediated and Insulin-Mediated Glucose Disposal in Insulin-Dependent Diabetes" Metabolism, vol. 41, No. 6, pp. 671-677, Jun. 1992, W.B. Saunders Company.
Wang, et al., "A Simple High-Performance Liquid Chromatography Assay for Simultaneous Determination of Plasma Norepinephrine, Epinephrine, Dopamine and 3,4-Dihydroxyphenyl Acetic Acid" Journal of Pharmaceutical and Biomedical Analysis, vol. 21, pp. 519-525, 1999, Elsevier Science B.V.
Weglicki, et al., "Potassium, Magnesium, and Electrolyte Imbalance and Complications in Disease Management" Clinical and Experimental Hypertension, vol. 1, pp. 95-112, 2005, Taylor & Francis, Inc.
Weindling, "Epinephrine Treatment in Hypotensive Newborns" ACTA Paediatrica, vol. 91, pp. 500-502, 2002.
Wendt, et al., "Intracerebral Hemorrhage Following Epinephrine Application for Anaphylactic Reaction" Clinical Neurology and Neurosurgery, letter to the editor, vol. 113, pp. 699-702, 2011, Elsevier.
Whyte, et al., "The Effect of Diuretic Therapy on Adrenaline-Induced Hypokalaemia and Hypomagnesaemia" European Journal of Clinical Pharmacology, vol. 34, pp. 333-337, 1988, Springer-Verlag.
Wilkie, et al., "Age-Related Changes in Venous Catecholamines Basally and During Epinephrine Infusion in Man" Journal of Gerontology, vol. 40, No. 2, pp. 133-140, 1985, The Gerontological Society of America.
Wilson, et al., "Septic Shock: Does Adrenaline Have a Role as a First-Line Inotropic Agent?" Anaesthesia and Intensive Care, vol. 20, pp. 470-474, 1992.
Wu, "Arterial Injection of Adrenaline Causing Severe Hypertension During Emergency Gastroscopy" Anaesthesia & Intensive Care, vol. 41, No. 5, p. 689, Sep. 2013.
Wu, et al., "Hemodynamics Effects of Epinephrine in Healthy and Hemorrhagic Shock Rats" Current Therapeutic Research, vol. 72, No. 6, Dec. 2011, Elsevier.
Wutrich, et al., "Early Increase In Arterial Lactate Concentration Under Epinephrine Infusion is Associated With a Better Prognosis During Shock" SHOCK, vol. 34, No. 1, pp. 4-9, 2010.
Xu, et al., "Renalase is a Novel, Soluble Monamine Oxidase that Regulates Cardiac Function and Blood Pressure" The Journal of Clinical Investigation, vol. 115, No. 5, pp. 1275-1280, May 2005.
Yakaitis, et al., "Relative Importance of alpha and beta Adrenergic Receptors During Resuscitation" Critical Care Medicine, vol. 7, No. 7, pp. 293-296, Jul. 1979, the Williams & Wilkins Co.
Yu, et al., "The Calcification of Elastic Fiber" Journal of Atherosclerosis Research, vol. 5, pp. 159-173, 1965.
Zanotti-Cavazzoni, "Hypertensive Crises" Critical Care Cardiovascular Disease, Part II, Chapter 35, pp. 723-733.
Zhang, et al., "Ultra Sensitive Measurement of Endogenous Epinephrine and Norepinephrine in Human Plasma by Semi-Automated SPE-LC-MS/MS" Journal of Chromatography B, vol. 895-896, pp. 186-190, 2012, Elsevier.
Zhou, et al., "Effects of Norepinephrine, Epinephrine, and Norepinephrine-Dobutamine on Systemic and Gastric Mucosal Oxygenation in Septic Shock" ACTA Pharmacol, vol. 23, No. 7, pp. 654-658, Jul. 2002.
Belcher Pharm, LLC., v. Hospira, Inc. Case No. 17-cv-775-LPS, document JTX-083, Feb. 7, 2013 Food and Drug Administration filing communication in regards to Mr. Taneja New Drug Application (6 pages).
Belcher Pharm, LLC., v. Hospira, Inc. Case No. 17-cv-775-LPS, document JTX-094, Oct. 4-17, 2013, e-mail communications between Belcher Pharmaceuticals and Sintetica SA (6 pages).
BBelcher Pharm, LLC. v. Hospira, Inc. Case No. 17-cv-775-LPS, document DTX-137, 2019, New Drug Application submitted to the Food and Drug Administration on Nov. 30, 2012 (58 pages).
Belcher Pharm., LLC. v. Hospira, Inc. Case No. 17-cv-775-LPS, document DTX-149, Response to "Complete Response Letter" dated Oct. 4, 2013 on NDA 205029 (38 pages).
Belcher Pharm, LLC. v. Hospira, Inc. Case No. 17-cv-775-LPS, document JTX-033, Epinephrine Injection, USP, 1:1000 (1 mg/mL), product label, Hospira, 2004, 2 pages.
Belcher Pharm, LLC. v. Hospira, Inc. Case No. 17-cv-775-LPS, document JTX-059, New Drug Application for Epinephrine injection, USP 1:1000 (41 pages).
Belcher Pharm, LLC. v. Hospira, Inc. Case No. 17-cv-775-LPS, document JTX-061, dated Mar. 8, 2013, Letter from Belcher Pharmaceutical to Food and Drug Administration dated Mar. 8, 2013 re New Drug Application 205029 (42 pages).
Belcher Pharm, LLC. v. Hospira, Inc. Case No. 17-cv-775-LPS, document JTX-063, Quality Information Amendment re New Drug Application 205029 (18 pages).
Belcher Pharm, LLC. v. Hospira, Inc. Case No. 17-cv-775-LPS, document JTX-077, Apr. 2006, Epinephrine Injection, USP 1:1000, product label, CURA Pharmaceutical Company Inc. (4 pages).
Belcher Pharm, LLC. v. Hospira, Inc. Case No. 17-cv-775-LPS, document JTX-088, Oct. 4, 2013 complete response letter from Food and Drug Administration re New Drug Application 205029 (31 pages).
Belcher Pharm, LLC. v. Hospira, Inc. Case No. 17-cv-775-LPS, document JTX-093, Oct. 4-14, 2013, FDA complete response letter and e-mails between Belcher Pharmaceuticals and Sintetica (42 pages).
Belcher Pharm, LLC. v. Hospira, Inc. Case No. 17-cv-775-LPS, document JTX-095, Oct. 4-18, 2013, e-mails between Belcher Pharmaceuticals and Sintetica (8 pages).
Belcher Pharm, LLC. v. Hospira, Inc. Case No. 17-cv-775-LPS, document JTX-105, Dec. 9, 2013-Jan. 9, 2014, e-mails between Belcher Pharmaceuticals and Sintetica (24 pages).

(56) References Cited

OTHER PUBLICATIONS

*Belcher Pharm, LLC.* v. *Hospira, Inc.* Case No. 17-cv-775-LPS, document JTX-107, Dec. 6, 2013-Jan. 16, 2014, e-mails between Belcher Pharmaceuticals and Sintetica (8 pages).
*Belcher Pharm, LLC.* v. *Hospira, Inc.* Case No. 17-cv-775-LPS, document DTX-118, Epinephrine Injection USP, 1mg/ML (1:1,000) ampule for IV Infusion, drug label, Belcher Pharmaceuticals, Jul. 2014 (8 pages).
*Belcher Pharm, LLC.* v. *Hospira, Inc.* Case No. 17-cv-775-LPS, document JTX-042, dated Nov. 25, 2013, The United States Pharmacopeia; The National Formulary, USP 37, NF 32, Vo. 2, pp. 2807.
Plaintiff *Belcher Pharmaceuticals, LLC* v. Defendant *Hospira, Inc.*, document 226, defendant proposed findings of fact, C.A. No. 17-175-LPS, dated Jul. 19, 2019 (47 pages).
Plaintiff *Belcher Pharmaceuticals, LLC* v. Defendant *Hospira, Inc.*, document 228, plaintiff's opening post-trial brief, C.A. No. 17-175-LPS, dated Jul. 19, 2019 (20 pages).
Plaintiff *Belcher Pharmaceuticals, LLC* v. Defendant *Hospira, Inc.*, document 229, plaintiff's proposed findings of fact, C.A. No. 17-175-LPS, dated Jul. 19, 2019 (18 pages).
Plaintiff *Belcher Pharmaceuticals, LLC* v. Defendant *Hospira, Inc.*, document 233, plaintiff's supplemental proposed findings of fact, C.A. No. 17-175-LPS, dated Aug. 19, 2019 (31 pages).
Plaintiff *Belcher Pharmaceuticals, LLC* v. Defendant *Hospira, Inc.*, document 237, defendant's reply post-trial brief, C.A. No. 17-175-LPS, dated Aug. 23, 2019 (26 pages).
Epinephrine-epinephrine injection, solution, product label, Hospira Inc., Lake Forest, IL, Sep. 2017.
Plaintiff *Belcher Pharmaceuticals, LLC* v. Defendant *Hospira, Inc.*, opening expert report of Rodolfo Pinal, PhD., C.A. No. 17-175-LPS, dated Feb. 22, 2019 (110 pages).
Plaintiff *Belcher Pharmaceuticals, LLC* v. Defendant *Hospira, Inc.*, expert Yeport of Shyam Mohapatra, Ph.D. in support of Belcher Pharmaceuticals, LLC infringement position, C.A. No. 17-175-LPS, dated Mar. 8, 2019 (33 pages).
U.S. District Court for the District of Delaware Plaintiff *Belcher Pharmaceuticals, LLC*, Defendant *Hospira, Inc.*, Case No. 17-775-LPS, Jun. 19, 2019, Bench Trial-vol. A, proceedings, 312 pages.
U.S. District Court for the District of Delaware Plaintiff *Belcher Pharmaceuticals, LLC*, Defendant *Hospira, Inc.*, Case No. 17-775-LPS, Jun. 20, 2019, Bench Trial—vol. B, proceedings, 164 pages.
"Product Quality Review(s)" application No. 207534QRIG1s000, Center for Drug Evaluation and Research, Feb. 18, 2016.
SYMJEPI—Epinephrine Injection, product label, Jun. 2017, Adamis Pharmaceuticals Corporation, 21 pages.
Allgire, et al., "High-Performance Liquid Chromatographic Determination of d-/l-Epinephrine Enantomer Ratio in Lodocaine-Epinephrine Local Anesthetics", Journal of Chromatography, vol. 325, pp. 249-254, 1985, Elsevier Science Publishers B.V., Amsterdam.
U.S. District Court for the District of Delaware Plaintiff *Belcher Pharmaceuticals, LLC*, Defendant *Hospira, Inc.*, Case No. 17-775-LPS, document 244, Bench Trial Opinion, Mar. 31, 2020.
"Pharmaceutical Development Q8(R2)", ICH Harmonised Tripartite Guideline, step 4 version, Aug. 2009, 28 page, International Conference on Harmonisation of Technical Requirements for Registration of Pharmaceuticals for Human Use.
Epinephrine Injection, USP, drug label, International Medication Systems, LTD, So. El Monte, CA, document 12, C.A. 1:18-cv-00960-LPS-CJB, filed Jul. 27, 2018.

U.S. District Court for the District of Delaware "Plaintiff's Belcher Pharmaceuticals, LLC, Unopposed Motion to Stay Pending Reissuance of the '700 and '728 Patents", Case No. 19-1854-RGA, 4 pages.
In The U.S. Court of Appeals for the Federal Circuit, Appeal from the United States District Court for the District of Delaware, Brief of the Appellant Belcher Pharmaceuticals, LLC, Case 20-1799, Document 15, filed Aug. 13, 2020, 149 pages.
"Bupivacaine Hydrochloride-bupivacaine hydrochloride injection, solution; Bupivacaine Hydrochloride And Epinephrine-bupivacaine hydrochloride and epinephrine injection, solution" product Tabel, Jul. 2016, Hospira, Inc.
"Septocaine and Epinephrine—articaine hydrochloride and epinephrine bitartrate injection, solution", product label, Feb. 2011, 17 pages, Septodont Inc.
"Bupivacaine—bupivacaine hydrochloride injection, solution" product Tabel, Jan. 2016, 12 pages, Hospira, Inc.
"Marcaine-bupicacaine hydrochloride injection, solution; Marcaine With Epinephrine—bupivacaine hydrochloride and epinephrine bitartrate injection, solution" product label, Jul. 2015, 26 pages, Hospira, Inc.
"Pain Control Products Reference Guide" Regional Anesthesia and Acute Pain Management Solutions, Q3 2015, 18 pages, B. Braun.
"Xylocaine; For Infiltration and Nerve Block" product label, Feb. 2015, 38 pages, Fresenius Kabi USA, LLC.
Richards, Jeremy et al., "Diagnosis and Management of Shock In The Emergency Department", Emergency Medicine Practice, vol. 16, No. 3, pp. 24 pages, Mar. 2014.
In The U.S. Court of Appeals for the Federal Circuit, Appeal from the United States District Court for the District of Delaware, Reply Brief of the Appellant Belcher Pharmaceuticals, LLC, Case 20-1799, Document 22, filed Oct. 13, 2020, 35 pages.
In The U.S. Court of Appeals for the Federal Circuit, Appeal from the United States District Court for the District of Delaware, Responsive Brief of Defendant-Appellee Hospira, Inc., Case 20-1799, Document 19, filed Sep. 22, 2020, 72 pages.
Epinephrine-epinephrine injection, solution, product label, Revised Nov. 2018, Hospira Inc., Lake Forest, IL.
"Epinephrine; Official Monographs", The United States Pharmacopeia The National Formulary, USP 32, NF27, vol. 2, May 1, 2009.
Dellinger, et al., "Surviving Sepsis Campaign Guidelines for Management of Severe Sepsis and Septic Shock", Critical Care Medicine, vol. 32, No. 3, pp. 858-873, Mar. 2004, Society of Critical Care Medicine.
Grünert, et al., "The action of ultraviolet and visible light on drugs from the phenylalkylamine series with regard to their stability in plastic containers", The Pharmacy, 1982, vol. 37, No. 11, VEB Verlag Volk und. Health Berlin, Berlin, Germany.
"Evidence-Based Outcomes Center; Recognition and Initial Management of Septic Shock", Texas Children's Hospital, Evidence-Based Guideline, 9 pages, Jan. 2017.
Brustugun, et al., "Photostability of epinephrine—The Influence of Bisulfite and Degradation Products", Pharmazie, vol. 59, pp. 457-463, 2004.
Rhodes, A. et al., "Surviving Sepsis Campaign: International Guidelines for Management of Sepsis and Septic Shock", Intensive Care Medicine, vol. 43, pp. 304-377, 2017, Springer.
"Epinephrine—epinephrine injection, solution, concentrate" product Tabel, Belcher Pharmaceuticals, LLC, revised Dec. 2020, 17 pages.
"EPIPEN® and EPIPEN Jr®" highlights of prescribing information, revised May 2016, 21 pages, Meridian Medical Technologies.
Schroeter, et al., "A Kinetic Study of Acid-Catalyzed Racemization of Epinephrine", Journal of the American Pharmaceutical Association, vol. XLVIII, No. 6, pp. 426-430, Jun. 1958.

\* cited by examiner

MORE POTENT AND LESS TOXIC FORMULATIONS OF EPINEPHRINE AND METHODS OF MEDICAL USE

RELATED APPLICATION

The present application is a continuation-in-part of pending U.S. patent application Ser. No. 15/616,157 filed Jun. 7, 2017, which is a continuation-in-part of pending U.S. patent application Ser. No. 15/596,440 filed May 16, 2017, the subject matter of which applications is incorporated herein by reference.

FIELD OF THE INVENTION

The present invention provides pharmaceutical formulations of levorotatory-epinephrine, l-epinephrine, more potent and less toxic than existing pharmaceutical formulations of epinephrine, along with methods of producing and using these pharmaceutical formulations of l-epinephrine, including preventing and or treating hypotension and hemostasis under surgical anesthesia.

BACKGROUND OF THE INVENTION

Epinephrine has a long history of pharmaceutical use that spans many decades since this catecholamine was first chemically synthesized at the turn of the twentieth century. Epinephrine is a sympathomimetic drug that acts on both alpha and beta adrenergic receptors found ubiquitously throughout much of the body. Epinephrine has profound effects on the cardiovascular system. Epinephrine has direct myocardial stimulation that increases the strength of ventricular contraction and cardiac output, positive inotropic action; increases heart rate, positive chronotropic action; and causes vasoconstriction in the veins and many vascular beds, positive vasopressor action. Epinephrine remains the first-line inotrope/vasopressor in many parts of the world and is recognized by the World Health Organization as an essential medicine with many medical uses and forms of administration.

As eye drops, epinephrine provides mydriasis, the dilation of the pupil, during intraocular surgery. As a solution for nebulization, epinephrine provides bronchodilation and relief of bronchospasm to asthmatics and those with chronic obstructive pulmonary disease. As a solution combined with analgesics for injection, including lidocaine for dental applications and bupivacaine for epidural analgesia, epinephrine improves and lengthens pain relief and sensory blockade during surgical procedures. Yet, epinephrine has many life saving uses in emergency room settings. As a solution for intramuscular or subcutaneous injection, epinephrine helps alleviate vasodilation, loss of intravascular fluid volume, hypotension, bronchospasm, and other symptoms associated with anaphylaxis, severe allergic reactions. Injections of epinephrine can also help stop bleeding, such as bleeding associated with peptic ulcers and surgical procedures. As a solution for intravenous injection, epinephrine is used as a critical adjunct in the treatment of cardiac arrest, e.g., to provide return of spontaneous circulation. Lastly, intravenous injection of this vasopressor provides critical care relief of hypotension associated with certain types of shock and fluid refractory shock, including septic shock, and relief of anaphylactic shock.

Although epinephrine has many uses, including many life saving uses, existing liquid formulations of epinephrine are associated with reduced potency, less desirable effects, or have the potential to cause harm. Formulations of epinephrine are plagued by two major problems, racemization and oxidation. Racemization is the enantiomeric conversion of l-epinephrine into its less biologically active dextrorotatory isoform, d-epinephrine, which has a significantly low pressor effect; about one-fifteenth that of l-epinephrine. The d-isoform may also affect adrenergic receptor subtypes differently than the l-isoform, resulting in substandard and undesirable effects. Because the United States Pharmacopeia, USP, monograph for epinephrine injection does not include specifications for d-epinephrine content, only total epinephrine content, manufacturers of epinephrine drug products are not required to test the chirality of their formulation and significant racemization occurs, thus leading to a less potent product with less desirable effects. In actuality, the d-epinephrine isoform should be classified as an impurity in an l-epinephrine drug product. It is believed that the epinephrine injection USP monograph does not include specifications for d-epinephrine because preventing its formation through racemization had proven too challenging. Whereas, oxidation of epinephrine can be prevented to a certain extent, including the use of antioxidants. The oxidation of epinephrine's alcohol group forms its less potent ketone form, known as adrenalone, which has little if any beta adrenergic activity. Racemization and oxidation of epinephrine are associated with reduced potency and less desirable effects as the impurities d-epinephrine and adrenalone form at the expense of l-epinephrine.

Drug manufacturers try to deal with the problem of oxidation by adding bisulfite antioxidants and increasing overages, both of which have the potential to cause harm to patients. Preservatives, such as sodium metabisulfite, are added to epinephrine formulations as antioxidants to reduce oxidation and to help keep formulations sterile. Sterilization techniques themselves often result in the loss of total epinephrine, and l-epinephrine, which may be compensated with increased overages. Sodium bisulfite and sodium metabisulfite, bisulfites, can cause mild to severe, life-threatening allergic reactions, including anaphylaxis or asthmatic episodes in susceptible individuals, especially those with sulfite sensitivities. So while epinephrine is indicated for treating anaphylaxis, the presence of sulfites in its formulation puts susceptible patients at great risk of exacerbating their anaphylaxis to the point of death. And for patients who are in other critical situations, such as cardiac arrest or septic shock, such sulfite reactions could greatly worsen the critical condition of these vulnerable patients. Most formulations also use overages of active pharmaceutical ingredient to compensate for degradation of epinephrine content and activity over the course of the product's shelf-life. This results in epinephrine drug products released after manufacturing with a higher than expected activity, which could be hazardous to patients as causing higher infusion and injection doses, thereby increasing side effects such as tachycardia.

In addition to the degradants d-epinephrine and adrenalone, which have been mentioned to have little pharmacological activity compared with l-epinephrine, lesser other degradants include adrenochrome and adrenolotin. A potentially toxic impurity, epinephrine sulfonate, forms by sulfonation reaction in epinephrine drug products containing sulfites.

Due to the deficiencies in existing pharmaceutical formulations of l-epinephrine, the identity, strength, quality, purity, and/or potency of the drug product cannot be adequately assured, or neither can its safety. There exists a great need for a liquid formulation of l-epinephrine that is preferably both preservative-free and sulfite-free, with minimal overage, if any, and with minimal levels of degradants, including d-epinephrine, while maintaining a sterility guarantee.

There also exists a great need for prefilled syringes of 1-epinephrine, to deliver greater dose than an autoinjector would and because the cost of epinephrine autoinjectors are excessively high and cost prohibitive to most patients and institutions. Currently, there are no prefilled syringes of 1-epinephrine that have been approved for safety and efficacy by the Food and Drug Administration (FDA), and for instance, prefilled syringes of 1 mL of 1 mg per mL 1-epinephrine are not even available for use as unapproved drug products. The present invention provides for prefilled syringes of an at least 1 mL or an at least 1 mg injectable liquid pharmaceutical formulation of epinephrine having high 1-epinephrine content and also so that there are no issues of subpotency or harmful impurities with this more stable formulation.

Importantly, the present invention fulfills unmet medical need by providing methods of use, including treating patients with a prefilled syringe of 1-epinephrine, in a unique way of injecting into an intravenous fluid bag for continuous intravenous infusion. Formerly, epinephrine from unapproved drug products was transferred with loss or degradation from an ampule or vial to an intravenous bag or injected as bolus administration without an intravenous bag to a patient. There is nothing obvious about using a prefilled syringe in the method of continuous intravenous administration when prefilled syringes currently administer bolus doses of drugs and would teach against continuous intravenous administration. Therefore, the present invention fulfills an unmet medical need of providing high potency, high purity 1-epinephrine by continuous intravenous infusion for patients requiring hemodynamic support with nearly no loss or degradation of 1-epinephrine; thereby, providing new safer methods of medicinal use to achieve an improved standard of patient care.

DETAILED DESCRIPTION OF THE INVENTION

Past solutions of epinephrine have included a microbial preservative in order to assure the sterility of the drug product, even if the drug product was a single-use vial used immediately after opening. Sulfites were able to counter the oxidative behavior of epinephrine by reacting with residual oxygen in its container instead of reacting with epinephrine, and thus, sequestered the free oxygen. When dissolution of the epinephrine was carried out by means of addition of diluted hydrochloric acid, HCl, some excess of acid could maintain a low pH near 2.2 and slow the degradation of epinephrine, also by forming inactive sulphonic acid.

Improved methods of preparation of sulfite-free pharmaceutical formulations of epinephrine included the compounding of the drug substance, followed by initial filtration, filling and sterilization. In order to produce and assure a sterile pharmaceutical solution of epinephrine as a drug product for injectable use, and without including preservatives such as metabisulfites, terminal heat sterilization following filling and/or final filtration under aseptic conditions during filling must be employed.

The compounding step utilized an active 1-epinephrine pharmaceutical ingredient base, such as 1-epinephrine hydrochloride, USP. This compounding step was performed to place the solid/powder active pharmaceutical ingredient into aqueous solution. Water for injection was the solvent. Mixing alone will not bring 1-epinephrine into aqueous solution adequately. The pH of the solution must be lowered in order for the 1-epinephrine base to dissolve properly. The pH can be lowered with an acid, such as an organic acid, and preferably 1 Normal (1N) hydrochloric acid that serves as a dissolution agent and a pH adjuster. Since the final solution will be injected into patients, the tonicity of the solution must be increased with a tonicity agent. Although various tonicity agents can be employed, the present methods preferably employ the use of sodium chloride as a tonicity agent. The batch formula per mL was 1.1 mg epinephrine base as the drug substance, 8.6 mg sodium chloride as the tonicity agent, 7.26 g hydrochloric acid (1N) as the dissolution agent, additional hydrochloric acid (1N) as a pH adjuster to lower pH to 2.2 to 2.6, and 987.04 mg water for injection as a solvent. Ideally, the compounding step and subsequent filtration step were conducted under inert nitrogen atmosphere to help prevent exposure of epinephrine and its solution to oxygen. It can be seen from this batch formula that a high 10% overage of epinephrine base was used to compensate for degradation over time, when the desired final concentration is 1 mg/mL epinephrine.

The compounded solution of 1-epinephrine was then filtered, such as by a 0.22 micrometer filter and transferred to a sterilized, preferably glass, vessel. Filtration of the compounded solution removed any particulates, whether bacterial or undissolved ingredients.

The filtered solution of epinephrine was then filled into sterilized or sterile containers using sterilized filling equipment. Sterile containers included, but were not limited to, glass ampules, glass vials with caps, glass bottles with caps, and syringes to make prefilled syringes or autoinjectors. To help protect the epinephrine solution against oxidation since no metabisulfites were used in the formulation, the filling step was performed under an inert atmosphere of nitrogen that is essentially devoid of oxygen to reduce the residual oxygen content in the empty space of the filled container. This filling step could be performed under aseptic conditions along with additional filtration, such as by a 0.22 micrometer filter integrated with the filling equipment. Alternatively, or additionally, filled containers could be sterilized by heat, such as by using an autoclave or by steam sterilization. Terminal sterilization at a temperature above the boiling point of water, such terminal sterilization at 121° C., with overkill conditions assured sterility guarantee of the final drug product. For example, a $F_0$ of 10 minutes by means of a steered sterilization cycle was initially chosen to reduce the thermal stress on the epinephrine solution. Because thermal stress was not found to degrade epinephrine, overkill conditions of sterilization could be used. Degradation of epinephrine was found mainly attributed to exposure to oxygen, which was directly related to nitrogen purge accuracy during the production and filling phases, instead of thermal treatment.

The above steps described the overall manufacturing process in making a drug product of preservative-free, sulfite-free solution of epinephrine. Specifically, it was found that this process inclusive of a 10% overage and an in-process pH range of 2.2 to 2.6 produced an epinephrine solution that could support a shelf-life of a 2 mL glass ampule containing 1 mL epinephrine solution for at least 48 months when studied in a climatic chamber at 25° C. for a maximum storage time of 60 months, in a climatic chamber at 30° C. for a maximum storage time of 12 months, and in a climatic chamber at 40° C. for a maximum storage time of 6 months.

However, this drug product produced by this manufacturing process with an in-process pH of approximately 2.5 was found to be inferior, and not only because of its high 10% overage. It was decided to test this epinephrine solution for d-epinephrine content even though there is no such rationale by USP or the industry to do so. When tested for d-epinephrine content by a chiral HPLC analytical method, it was unexpectedly found that approximately 14% of the l-epinephrine had been racemized into d-epinephrine at the product's release. After storage at 25° C. for 6 months, at least 19% of the l-epinephrine was converted to d-epinephrine. The drug product produced in this manner would contain less than 90% l-epinephrine in well under a year, and for all practical purposes, was unsuitable for use.

Producing an epinephrine drug product with a high l-epinephrine content, such as greater than 90%, throughout its shelf-life of over one year seemed impossible in a preservative-free, sulfite-free solution, and had never been accomplished before. Increasing overages above 10% was not a viable solution. Terminal sterilization of the epinephrine solution only contributed to about 4% racemization, so eliminating heat sterilization and depending solely on aseptic filtration would not solve the racemization problem, nor have as strong of a final sterility guarantee in this antimicrobial-free solution. Lowering the in-process pH was not believed possible due to oxidation issues. The lower the pH was to 2.2, the lower the impact was of potential oxygen residues in the solution. The thought of raising the in-process pH above the 2.2-2.6 of previous methods, and allowing for additional oxidation in an antioxidant-free solution, was contradictory to one skilled in the art.

Inadvertently, increasing the in-process pH to 2.8-3.3, unexpectedly reduced the racemization of l-epinephrine to d-epinephrine at release by approximately two-thirds, from 14% to 5%, respectively. To the contrary, these results led to the discovery that in a preservative-free, sulfite-free, l-epinephrine solution, racemization was a more significant problem than expected, even more so than oxidation. This discovery led to new methods of manufacturing sulfite-free, l-epinephrine solution with an in-process pH of 2.8 to 3.3, approximately 3.0, which was a nonobvious solution to the problem of racemization. Most importantly, with these new methods, overages could greatly be reduced.

The new method of preparing a 1 mg/mL solution of l-epinephrine, such as in a glass ampule, has a revised batch formula per mL of: approximately 1.03 mg epinephrine base, as the drug substance, 8.6 mg sodium chloride as the tonicity agent, 7.26 g hydrochloric acid (1N) as the dissolution agent, additional hydrochloric acid (1N) as a pH adjuster to lower pH only to 2.8 to 3.3, and 987.11 mg water for injection as a solvent. The compounding of the drug substance, followed by initial filtration, filling and sterilization are all conducted under inert nitrogen atmosphere to help prevent exposure of epinephrine and its solution to oxygen.

With less than or no more than a 6% overage, and preferably a 3% overage, a viable shelf-life of at least one year, e.g., at least 15 months, was achieved with the new method with more than 90% l-epinephrine content at the end of the shelf-life. A sealed 2 mL glass ampule served as the container for the 1 mL drug product that was tested. However, the drug product solution of the present invention can be made in larger volumes in other sterile containers, including glass vials and bottles, and syringes and autoinjectors; including autoinjectors conducive with the preservative-free formulation. The new and improved formulation with reduced overage also has less than or no more than 6.5% total impurities, including less than or no more than 6% d-epinephrine and less than or no more than 0.5% adrenalone at release; and less than or no more than 12.5% total impurities, including less than or no more than 12% d-epinephrine and less than or no more than 0.5% adrenalone through a shelf-life of at least 12 months, and preferably through a shelf-life of at least 15 months. If aseptic filtration is used without terminal sterilization, these new methods would allow an l-epinephrine drug product to be prepared without any overage of epinephrine base, so that exactly 1.00 mg of epinephrine base is used per mL in the compounding step.

These inventive methods have discovered and achieved new limits for an injectable liquid pharmaceutical formulation of l-epinephrine sterile solution; less than or no more than about 6% d-epinephrine at release, and less than or no more than about 12% d-epinephrine through a shelf-life of at least 12 months; which has never been accomplished before, even if preservatives/sulfites are optionally included in the formulation as alternate embodiments (e.g., preservatives/sulfites up to about 1 mg per mL, such as sodium metabisulfite). Although these injectable liquid pharmaceutical formulations of l-epinephrine sterile solution introduced by this invention can be produced having any desirable concentration of l-epinephrine, they are preferably compounded in an aqueous solution as approximately 1.0 to 1.06 mg/mL l-epinephrine, and further include a tonicity agent, and include no more than about 6% d-epinephrine and no more than about 0.5% adrenalone at release, and no more than about 12% d-epinephrine and no more than about 0.5% adrenalone over a shelf-life of at least 12 months. Such injectable liquid pharmaceutical formulations of l-epinephrine sterile solution taught by this invention have uncompromised potency of l-epinephrine at release and through their shelf-life.

The present invention therefore provides improved methods of formulating safer and more reliable pharmaceutical preparations of epinephrine for medicinal use. Unlike other epinephrine formulations, these improved formulations are preservative-free and sulfite-free so that there are no safety issues for anaphylaxis and no toxic epinephrine sulfonate byproducts. These improved epinephrine formulations have no need for high overages, and use minimal overages, if any to assure reliable dosage. The present methods of this invention preferably use l-epinephrine hydrochloride, USP as the active pharmaceutical ingredient base, although other l-epinephrine active ingredients and salts and combinations thereof can be employed, including epinephrine bitartrate. The present methods of this invention preferably use sterile containers including, but not limited to, glass ampules, glass vials with caps, glass bottles with caps, and syringes to make prefilled syringes or autoinjectors. Other inert gases, instead of or in addition to nitrogen, can be used for the manufacturing process. Other concentrations of sulfite-free, l-epinephrine solution greater or lower than approximately 1 mg/mL can also be prepared using these new methods and in-process pH under nitrogen (inert gas) atmosphere, where nitrogen (inert gas) purge accuracy is inversely related to oxygen exposure during the production and filling phases.

The present invention also includes methods of using these more potent and less toxic liquid formulations of l-epinephrine as eye drops to provide mydriasis during intraocular surgery; as a solution for nebulization to provide bronchodilation and relief of bronchospasm to asthmatics and those with chronic obstructive pulmonary disease; as a solution combined with analgesics for injection, including lidocaine for dental applications and tumescent anesthesia and tumescent liposuction; and bupivacaine for epidural analgesia, to improve and lengthen pain relief and sensory blockade during surgical procedures; as a solution for intramuscular or subcutaneous injection to counter symptoms associated with anaphylaxis or to help stop bleeding associated with peptic ulcers and surgical procedures; as a solution for intravenous injection in the treatment of cardiac arrest, to provide return of spontaneous circulation; and as a solution for intravenous injection to relieve hypotension associated with certain types of shock and fluid refractory shock, including septic shock.

Anaphylaxis is a severe allergic reaction with rapid onset that can result in death. Symptoms include rash, swelling in the throat or tongue, shortness of breath, vomiting, dizziness, and importantly, low blood pressure. Severe or untreated anaphylaxis can lead to anaphylactic shock, a state in which the drop in blood pressure causes inadequate blood perfusion to tissues, resulting in cellular and tissue damage and organ failure that can lead to death. The trigger for anaphylaxis can be exposure to a certain food or drug, an insect sting, or can be brought on by exercise. Other times, the cause of anaphylaxis is unknown; is idiopathic.

The primary treatment for anaphylaxis is injection of epinephrine, by bolus intravenous, intramuscular, or subcutaneous injection. With both alpha- and beta-adrenergic effects, epinephrine serves as a vasotropic agent that constricts blood vessels to offset the vasodilation brought on by anaphylaxis so as to restore adequate blood pressure. Epinephrine also serves as an inotropic agent that increases heart rate. Epinephrine's beta-adrenergic effects relieve difficulty in breathing by relaxing bronchial tissue in the lungs as a bronchodilator. Epinephrine may also alleviate itching, swelling, and tissue edema.

Autoinjectors have made intramuscular and subcutaneous injection of epinephrine easier and more convenient to patients as such epinephrine injections can be self-administered and portable for travel.

Sulfites (e.g., sodium bisulfite, sodium metabisulfite, sodium sulfite, potassium bisulfite, and potassium metabisulfite) are chemicals added to foods and drugs as an anti-oxidant or preservative. Interestingly, the symptoms of anaphylaxis mirror those of sulfite-sensitivity or sulfite-allergy: bronchoconstriction, hypotension, dyspnea, urticaria, laryngeal edema, itching and swelling, and even shock. Sometimes a patient can be known to be sulfite-sensitive or sulfite-allergic. Other times, sulfite-sensitivity or sulfite-allergy can happen in a patient not known to be sulfite-sensitive or sulfite-allergic. It is thought that asthmatics generally have a higher predisposition sulfite-sensitivity or sulfite-allergy. Studies have demonstrated that sulfites may cause allergic-type reactions in certain susceptible persons, especially asthmatics. The term sulfite-sensitivity is sometimes used interchangeably with sulfite-allergy, but is more correctly used instead of sulfite-allergy when immunoglobulins to sulfites have not been detected. There are many theories to the mechanism of sulfite-sensitivity. Regardless of which theory proves true, individuals have died from eating at salad bars due to foods being sprayed with sulfites. Medications containing sulfites also place some patients at great risk.

The FDA requires a sulfite warning in the label of sulfite-containing prescription drug products, which also mentions the uncertainty of who may have sulfite-allergy. The prescription drug label must mention which sulfite it contains, a sulfite that may cause allergic-type reactions including anaphylactic symptoms and life-threatening or less severe asthmatic episodes in certain susceptible people.

Ironically, current autoinjectors of epinephrine on the market to treat anaphylaxis contain sulfites. If the patient turns out to have a sulfite-sensitivity or sulfite-allergy, the anaphylactic symptoms may decrease from the epinephrine, then suddenly reappear from reaction to sulfites in the formulation. This may result in a prolonged cycle of extra epinephrine injections, because the sulfites may cause or exacerbate the anaphylaxis, making the anaphylaxis more severe or life-threatening. The time between recurrence of symptoms may give a false sense of security as patients may believe the sulfite-containing epinephrine autoinjector cured their anaphylaxis, only to have anaphylaxis return from sulfite-sensitivity an hour or so later. During this window, the patient may be away from a hospital or be without additional autoinjectors, and therefore, be in danger when symptoms reoccur and their airways constrict.

Because there had not been any sulfite-free, epinephrine drug products approved by the FDA, physicians and patients were left without safer alternatives, because an alternative to using epinephrine in a life-threatening situation may not be satisfactory. Fortunately, the preservative-free and sulfite-free formulation of the present invention has been FDA approved, which is believed to provide a safer alternative in patients with known or unknown sulfite-sensitivity, and can be supplied in autoinjector form.

The present invention is a method of treating allergic reaction, anaphylaxis, anaphylactic shock, or a combination thereof by an injection of at least one dosage of an injectable liquid pharmaceutical formulation of preservative-free and sulfite-free 1-epinephrine sterile solution. The injectable liquid pharmaceutical formulation is compounded in an aqueous solution as approximately 1.0 to 1.06 mg/mL 1-epinephrine, and further includes a tonicity agent. The injectable liquid pharmaceutical formulation has a pH between 2.8 and 3.3. The liquid pharmaceutical formulation includes no more than about 6% d-epinephrine and no more than about 0.5% adrenalone at release, and no more than about 12% d-epinephrine and no more than about 0.5% adrenalone over a shelf-life of at least 12 months.

The injectable liquid pharmaceutical formulation is compounded in an aqueous solution preferably as 1.03 mg/mL 1-epinephrine.

The injectable liquid pharmaceutical formulation preferably has a concentration of 1 mg per mL 1-epinephrine.

The injectable liquid pharmaceutical formulation can be stored in a container with an inert gas prior to use.

The injection is preferably intramuscular or subcutaneous injection and is preferably administered by an autoinjector containing the injectable liquid pharmaceutical formulation.

The at least one dosage of an injectable liquid pharmaceutical formulation of preservative-free and sulfite-free, 1 mg per mL 1-epinephrine sterile solution is preferably and approximately 0.30 mg 1-epinephrine.

Alternatively, such as for pediatric patients, the at least one dosage of an injectable liquid pharmaceutical formulation of preservative-free and sulfite-free, 1 mg per mL 1-epinephrine sterile solution is approximately 0.15 mg 1-epinephrine.

For more severe cases, the at least one dosage of an injectable liquid pharmaceutical formulation of preservative-free and sulfite-free, 1 mg per mL 1-epinephrine sterile solution can be approximately 0.50 mg 1-epinephrine.

Importantly, the method of treating allergic reaction, anaphylaxis, anaphylactic shock, or a combination thereof is also performed in patients with known or unknown sulfite-sensitivity or sulfite-allergy. This method further prevents the exacerbation, extension, or recurrence of allergic reaction, anaphylaxis, anaphylactic shock, or a combination thereof caused by sulfite-sensitivity or sulfite-allergy by avoiding additional sulfite-exposure. Such additional sulfite-exposure which would otherwise come from sulfite-containing epinephrine products and autoinjectors.

In another method embodiment, the method is for treating allergic reaction, anaphylaxis, anaphylactic shock, or a combination thereof in a patient with known or unknown sulfite-sensitivity or sulfite-allergy by an intramuscular or subcutaneous injection of at least one 0.15 mg to 0.50 mg 1-epinephrine dosage of an injectable liquid pharmaceutical formulation of preservative-free and sulfite-free, 1 mg per mL 1-epinephrine sterile solution administered by an autoinjector containing the at least one dosage of the injectable liquid pharmaceutical formulation. The injectable liquid pharmaceutical formulation is compounded in an aqueous solution as approximately 1.0 to 1.06 mg/mL 1-epinephrine, and further includes a tonicity agent. The injectable liquid pharmaceutical formulation has a pH between 2.8 and 3.3. The liquid pharmaceutical formulation has no more than 6.5% total impurities at release, and no more than 12.5% total impurities over a shelf-life of at least 12 months.

The injectable liquid pharmaceutical formulation can be stored in a container with an inert gas prior to use.

The injectable liquid pharmaceutical formulation preferably has no more than 12.5% total impurities over a shelf-life of at least 15 months, including no more than 12% d-epinephrine and no more than 0.5% adrenalone.

The method can be applied specifically to patients whose anaphylaxis was triggered by sulfite exposure from other medications. The method of treating allergic reaction, anaphylaxis, anaphylactic shock, or a combination thereof that is caused by or exacerbated by sulfite exposure from sulfite-containing medications in a patient with known or unknown sulfite-sensitivity or sulfite-allergy; the method including an intramuscular or subcutaneous injection of at least one 0.15 mg to 0.50 mg 1-epinephrine dosage of an injectable liquid pharmaceutical formulation of preservative-free and sulfite-free, 1 mg per mL 1-epinephrine sterile solution administered by an autoinjector containing the at least one dosage of the injectable liquid pharmaceutical formulation. The injectable liquid pharmaceutical formulation is compounded in an aqueous solution as approximately 1.0 to 1.06 mg/mL 1-epinephrine, and further includes a tonicity agent. The injectable liquid pharmaceutical formulation has a pH between 2.8 and 3.3. The liquid pharmaceutical formulation has no more than 6.5% total impurities at release, and no more than 12.5% total impurities over a shelf-life of at least 12 months.

The method can also be applied specifically to patients whose anaphylaxis was triggered by sulfite exposure from a sulfite-containing autoinjector of epinephrine. The method of treating allergic reaction, anaphylaxis, anaphylactic shock, or a combination thereof that is caused by or exacerbated by sulfite exposure from a sulfite-containing epinephrine formulation administered by an autoinjector in a patient with known or unknown sulfite-sensitivity or sulfite-allergy; the method including an intramuscular or subcutaneous injection of at least one 0.15 mg to 0.50 mg 1-epinephrine dosage of an injectable liquid pharmaceutical formulation of preservative-free and sulfite-free, 1 mg per mL 1-epinephrine sterile solution administered by an autoinjector containing the at least one dosage of the injectable liquid pharmaceutical formulation. The injectable liquid pharmaceutical formulation is compounded in an aqueous solution as approximately 1.0 to 1.06 mg/mL 1-epinephrine, and further includes a tonicity agent. The injectable liquid pharmaceutical formulation has a pH between 2.8 and 3.3. The liquid pharmaceutical formulation has no more than 6.5% total impurities at release, and no more than 12.5% total impurities over a shelf-life of at least 12 months.

The invention is also, therefore, an autoinjector containing at least one 0.15 mg to 0.50 mg 1-epinephrine dosage of an injectable liquid pharmaceutical formulation of preservative-free and sulfite-free, 1 mg per mL 1-epinephrine sterile solution. The injectable liquid pharmaceutical formulation is compounded in an aqueous solution as approximately 1.0 to 1.06 mg/mL 1-epinephrine, and further includes a tonicity agent. The injectable liquid pharmaceutical formulation has a pH between 2.8 and 3.3. The liquid pharmaceutical formulation has no more than 6.5% total impurities at release, and no more than 12.5% total impurities over a shelf-life of at least 12 months. The autoinjector of the present invention is used for treating allergic reaction, anaphylaxis, anaphylactic shock, or a combination thereof in a patient with known or unknown sulfite-sensitivity or sulfite-allergy by providing an intramuscular or subcutaneous injection of the injectable liquid pharmaceutical formulation to the patient.

There also exists a great need for prefilled syringes of 1-epinephrine, to deliver greater dose than an autoinjector would and because the cost of epinephrine autoinjectors are excessively high and cost prohibitive to most patients and institutions. Currently, there are no prefilled syringes of 1-epinephrine approved for safety and efficacy by the Food and Drug Administration (FDA), and for instance, prefilled syringes of 1 mL of 1 mg per mL 1-epinephrine are not even available for use as unapproved drug products. The present invention provides for prefilled syringes of an at least 1 mL or 1 mg injectable liquid pharmaceutical formulation of epinephrine having high 1-epinephrine content and also so that there are no issues of subpotency or harmful impurities.

Importantly, the present invention fulfills unmet medical need by providing methods of use, including treating patients with a syringe or prefilled syringe of 1-epinephrine, in a unique way of injecting into an intravenous fluid bag for continuous intravenous infusion. Formerly, epinephrine from unapproved drug products was transferred with loss or degradation from an ampule or vial to an intravenous bag or injected as bolus administration without an intravenous bag to a patient. There is nothing obvious about using a prefilled syringe in the method of continuous intravenous administration when prefilled syringes currently administer bolus doses of drugs and would teach against continuous intravenous administration. Therefore, the present invention fulfills an unmet medical need of providing high potency, high purity 1-epinephrine by continuous intravenous infusion for patients requiring hemodynamic support with nearly no loss or degradation of 1-epinephrine; thereby, providing new safer methods of medicinal use to achieve an improved standard of patient care.

The present invention include a method of performing vasoconstriction and increasing perfusion or raising a blood pressure in a patient with a continuous intravenous infusion of epinephrine delivered via an intravenous fluid bag with an intravenous line and or an intravenous catheter. Generally, intravenous lines are connected to an intravenous catheter, the standard of infusion care; however, certain emergency situations may connect an intravenous line directly to a needle or butterfly needle for administration into a vein. Importantly, this method comprises the step of injecting a prefilled syringe of an at least 1 mL or 1 mg injectable liquid pharmaceutical formulation of epinephrine into this intravenous fluid bag or a medication port of this intravenous fluid bag. This method further comprises the diluting of epinephrine to a concentration less than 1 mg per 100 mL in this intravenous fluid bag during this continuous intravenous infusion of epinephrine. The method also or alternatively comprises increasing heart contraction and heart rate of the patient. The raising of a blood pressure in the patient is at least mean arterial pressure. The intravenous fluid bag initially contains a premixed saline solution of 50 mL to about 1000 mL. Usually this is 0.9% normal saline, sodium chloride solution. Ideally, the intravenous fluid bag initially contains a sugar and saline solution of 50 mL to about 1000 mL, and preferably this intravenous fluid bag initially contains 1000 mL of a premixed 5 percent dextrose and 0.9% sodium chloride-containing solution. The dextrose or sugar in the intravenous fluid bag helps prevent oxidation and or racemization of 1-epinephrine.

The at least one syringe or prefilled syringe of an at least 1 mL or 1 mg injectable liquid pharmaceutical formulation of epinephrine will either have a luer fitting or luer lock syringe tip that can insert into a medication port of the intravenous fluid bag or accept a needle that can be injected through the bag material or into the medication port of the intravenous fluid bag. Alternatively, the at least one syringe or prefilled syringe of an at least 1 mL or 1 mg injectable liquid pharmaceutical formulation of epinephrine is a staked needle syringe that can be injected through the bag material or into the medication port of the intravenous fluid bag. The at least one syringe or prefilled syringe of an at least 1 mL or 1 mg injectable liquid pharmaceutical formulation of epinephrine may be a standard glass, plastic, and or crystal zenith syringe that is manually injected, or may contain a vial or cartridge component.

The at least one syringe or prefilled syringe of an at least 1 mL or 1 mg injectable liquid pharmaceutical formulation of epinephrine preferably contains 1 mL of a 1 mg per mL concentration of epinephrine, such as may be of a glass 1 mL Long glass syringe. In other embodiments, the at least one syringe or prefilled syringe of an at least 1 mL or 1 mg injectable liquid pharmaceutical formulation of epinephrine preferably contains 10 mL of a 0.1 mg per mL concentration of epinephrine.

The at least one syringe or prefilled syringe of an at least 1 mL or 1 mg injectable liquid pharmaceutical formulation of epinephrine further has a ratio of 1-epinehrine:d-epinephrine greater than about 6:1 and preferably at least 9:1. When said at least one syringe or prefilled syringe of an at least 1 mL or 1 mg injectable liquid pharmaceutical formulation of epinephrine is injected into the at least one intravenous fluid bag, the ratio of ratio of 1-epinehrine:d-epinephrine in the intravenous fluid bag and or the continuous intravenous infusion is much greater than 4:1, even greater than about 6:1, and preferably is at least 9:1. Because of sulfite-sensitivity, which is usually unknown to most patients, the at least one syringe or prefilled syringe of an at least 1 mL or 1 mg injectable liquid pharmaceutical formulation of epinephrine is preferably preservative-free and or sulfite-free; which is technically challenging to maintaining the high 1-epinephrine:d-epinephrine ratio since oxidation and racemization would otherwise occur.

In some instances, the at least one container or prefilled syringe of an at least 1 mL or 1 mg injectable liquid pharmaceutical formulation of epinephrine is terminally heat sterilized. But it was uniquely found that terminal heat sterilization can be avoided under certain conditions if no terminal sterilization is used, or if irradiating sterilization, such as gamma-sterilization, or ethylene oxide sterilization is used and compatible with certain syringe components.

Importantly, the invention also includes methods of producing and using these pharmaceutical formulations of 1-epinephrine, including preventing and or treating hypotension and hemostasis under surgical anesthesia.

The invention is a method of treating hypotension in a patient having or recovering from invasive orthopedic or gynecological procedures, surgery, or a combination thereof. These types of invasive orthopedic or gynecological procedures or surgery can include, but are not limited to, knee replacement surgery, hip replacement surgery, hysterectomy, and even procedures of or during child birth or cesarean section. Such hypotension can be the result of the invasive procedure or surgery itself, such as but not limited to bleeding, and or, a side effect of one or more anesthetic agents. Anesthetic agents can include, but are not limited to, amide anesthetics such as lidocaine, prilocaine, bupivicaine, chloroprocaine; barbiturates; benzodiazepines; ketamine; propofol; and many others. The method includes a continuous intravenous infusion of 1-epinephrine delivered via an at least one intravenous fluid bag with an at least one intravenous line and or an at least one intravenous catheter following a step of injecting said patient with an at least 1 microgram per mL solution of 1-epinephrine in saline and or anesthetic into a subarachnoid space, epidural space, or a combination thereof to prolong anesthesia. The at least one intravenous fluid bag contains up to 1,000 mL of a dextrose and or saline-containing solution. The method comprises the step of injecting an at least one syringe of a 1 mg injectable liquid pharmaceutical formulation of 1-epinephrine into each said at least one intravenous fluid bag or medication port thereof; this at least one syringe of a 1 mg injectable liquid pharmaceutical formulation of 1-epinephrine includes a tonicity agent and has no more than 12.5% total impurities or no more than 12% d-epinephrine. The method further comprises the diluting of 1-epinephrine to a concentration of about 1 microgram per mL in each said at least one said intravenous fluid bag during said continuous intravenous infusion of 1-epinephrine. The method optionally comprises protecting the at least one said intravenous fluid bag from light or UV-radiation after said step of injecting said syringe into said at least one intravenous fluid bag or medication port thereof to prevent 1-epinephrine degradation and impurities from forming so that the continuous intravenous infusion of 1-epinephrine has a ratio of 1-epinephrine:d-epinephrine greater than 4:1 to treat hypotension effectively.

The invention also is a method of preventing and or treating cardiac arrhythmias and hypotension in a patient having or recovering from invasive orthopedic or gynecological procedures, surgery, or a combination thereof. A unique situation exists when a patient undergoes surgery under general anesthesia (e.g., by inhalation) with general anesthetic agents containing halogenated hydrocarbons (e.g., halothane, desflurane) or cyclopropane. If such anesthetic agents are used, and the patient experiences hypotension as a result of the surgery itself and or as a side effect to the general anesthetic, then epinephrine cannot be used to treat the hypotension because these agents can sensitize the heart to epinephrine. Therefore, the method includes a step of replacing general anesthesia with regional anesthesia, so that pain can be treated, but without the general anesthetic agents. The method further including a step of injecting the patient with an at least 1 microgram per mL of 1-epinephrine in anesthetic solution into a subarachnoid space, epidural space, or a combination thereof to treat or prevent pain. The at least 1 microgram per mL of 1-epinephrine in anesthetic solution is prepared just prior to said step of injecting into said subarachnoid space, epidural space, or a combination thereof by mixing at least some of a 1 mg injectable liquid pharmaceutical formulation of 1-epinephrine including a tonicity agent and having no more than 12.5% total impurities or no more than 12% d-epinephrine with at least some of an anesthetic solution. The method further includes a step of providing the patient with a continuous intravenous infusion of 1-epinephrine delivered via an at least one intravenous fluid bag with an at least one intravenous line and or an at least one intravenous catheter; the at least one intravenous fluid bag containing up to 1,000 mL of a dextrose and or saline-containing solution; the method comprising the step of injecting an at least one syringe of a 1 mg injectable liquid pharmaceutical formulation of 1-epinephrine into each said at least one intravenous fluid bag or medication port thereof; said at least one syringe of a 1 mg injectable liquid pharmaceutical formulation of 1-epinephrine including a tonicity agent and having no more than 12.5% total impurities or no more than 12% d-epinephrine. The method further comprises the diluting of 1-epinephrine to a concentration of about 1 microgram per mL in each said at least one said intravenous fluid bag during said continuous intravenous infusion of 1-epinephrine. The method optionally comprises protecting the at least one said intravenous fluid bag from light or UV-radiation after said step of injecting said syringe into said at least one intravenous fluid bag or medication port thereof to prevent 1-epinephrine degradation and impurities from forming so that said continuous intravenous infusion of 1-epinephrine has a ratio of 1-epinephrine:d-epinephrine greater than 4:1.

The invention is also a method of providing hemostasis to a patient while having invasive orthopedic or gynecological surgery, or a combination thereof. The method includes a step of injecting said patient with an at least 1 microgram per mL of 1-epinephrine in anesthetic solution into a subarachnoid space, epidural space, or a combination thereof to treat or prevent pain during said invasive orthopedic or gynecological surgery. The at least 1 microgram per mL of 1-epinephrine in anesthetic solution is prepared just prior to said step of injecting into said subarachnoid space, epidural space, or a combination thereof by mixing at least some of a 1 mg injectable liquid pharmaceutical formulation of 1-epinephrine from an ampoule, syringe or prefilled syringe including a tonicity agent and having no more than 12.5% total impurities or no more than 12% d-epinephrine with at least some of an anesthetic solution. The method further includes a step of applying at least some of a 1 mg injectable liquid pharmaceutical formulation of 1-epinephrine to bleeding tissue from an ampoule, syringe or prefilled syringe and optionally applied using a sponge, clothe, or pad; the 1 mg injectable liquid pharmaceutical formulation of 1-epinephrine including a tonicity agent and having no more than 12.5% total impurities or no more than 12% d-epinephrine. This method stops or reduces surgical bleeding to the tissues.

The method optionally comprises protecting the at least one said intravenous fluid bag from light or UV-radiation after the step of injecting the prefilled syringe into the at least one intravenous fluid bag or medication port thereof to prevent epinephrine degradation and impurities from forming. A tinted and or opaque intravenous fluid bag is one unique option, but may be less desirable if the fluid cannot be checked for cloudiness or particulate matter, which can be harmful. Preferably, the method includes the step of covering at least one intravenous fluid bag with a light or UV-shielding material or clothe or bag to protect from exposure to light which could reduce the 1-epinephrine:d-epinephrine ratio and or increase impurity levels.

The method further comprises the diluting of epinephrine to a concentration less than 1 mg per 100 mL in this intravenous fluid bag during this continuous intravenous infusion of epinephrine to an ideal concentration of about 1 microgram per mL epinephrine.

The continuous intravenous infusion of epinephrine of this method is at an infusion rate of at least 0.04 micrograms of epinephrine per kg body weight per min and less than 3 micrograms of epinephrine per kg body weight per min, at one or more time points during this continuous intravenous infusion. The continuous intravenous infusion of epinephrine is at an infusion rate that is titrated up or down based on a the blood pressure of the patient to achieve the desired hemodynamic goals or to stabilize the patient's vital signs. The continuous intravenous infusion of epinephrine has an infusion rate that is incrementally adjusted by not more than 0.3 micrograms of epinephrine per kg body weight per min at a time so as to not overshoot desired hemodyamic or vital sign goals and or harm the patient.

In some instances, continuous intravenous infusion of epinephrine is maintained for at least half a day. In some instances, continuous intravenous infusion of epinephrine is weaned for at least half a day. For instance, treating a patient for septic shock may require a very long period of continuous intravenous infusion of epinephrine that could last more than one day. As such, this method provides for using multiple intravenous fluid bags injected with prefilled epinephrine syringes, sequentially. It can be envisioned in some circumstances, that multiple continuous intravenous infusions of epinephrine are needed with multiple intravenous fluid bags injected with prefilled epinephrine syringes simultaneously, as might be the case if a patient has circulatory blockages. The method allows for continuous intravenous infusion of epinephrine using more than one said intravenous fluid bag and more than one said prefilled syringe of an at least 1 mL or 1 mg injectable liquid pharmaceutical formulation of epinephrine.

The patient treated with this method is selected from patients having, developing, or recovering from a form of shock, septic shock, anaphylactic shock, myocardial infarction, or cardiac arrest; and or undergoing surgery.

A primary embodiment of the invention is a method of treating a patient having, developing, or recovering from a form of shock with a continuous intravenous infusion of epinephrine delivered via an at least one intravenous fluid bag with an at least one intravenous line and or an at least one intravenous catheter. The at least one intravenous fluid bag contains up to 1,000 mL of a dextrose and or saline-containing solution. The method comprises the step of injecting an at least one prefilled syringe of a 1 mg injectable liquid pharmaceutical formulation of epinephrine into each said at least one intravenous fluid bag or medication port thereof. The method further comprises the diluting of epinephrine to a concentration of about 1 microgram per mL in each at least one said intravenous fluid bag during the continuous intravenous infusion of epinephrine. The method optionally comprises protecting the at least one said intravenous fluid bag from light or UV-radiation after the step of injecting the prefilled syringe into the at least one intravenous fluid bag or medication port thereof to prevent epinephrine degradation and impurities from forming.

Another embodiment of the invention is a method of treating a patient having, developing, or recovering from septic shock or anaphylactic shock with a continuous intravenous infusion of epinephrine delivered via an at least one intravenous fluid bag with an at least one intravenous line and an at least one intravenous catheter. The at least one intravenous fluid bag contains up to 1,000 mL of a dextrose and or saline-containing solution, preferably 5 percent dextrose in 0.9 percent normal sodium chloride solution. The method comprises the step of injecting an at least one prefilled syringe of an at least 1 mL injectable liquid pharmaceutical formulation of epinephrine into each at least one intravenous fluid bag or medication port thereof. The method further comprising the diluting of epinephrine to a concentration of about 1 microgram per mL in each at least one intravenous fluid bag during said continuous intravenous infusion of epinephrine. The method optionally comprises protecting the at least one said intravenous fluid bag from light or UV-radiation after the step of injecting the prefilled syringe into the at least one intravenous fluid bag or medication port thereof to prevent epinephrine degradation and impurities from forming. The at least one intravenous fluid bag after injecting with the epinephrine prefilled syringe, and or the continuous intravenous infusion of epinephrine, have a ratio of 1-epinehrine:d-epinephrine greater than 4:1 and preferably at least 9:1.

Another embodiment of the invention is a method of treating a patient having, developing, or recovering from septic shock or anaphylactic shock with a continuous intravenous infusion of epinephrine delivered via an at least one intravenous fluid bag with an at least one intravenous line and an at least one intravenous catheter. The at least one intravenous fluid bag contains up to 1,000 mL of a dextrose and or saline-containing solution. The method comprises the step of injecting an at least one prefilled syringe of a 1 mg in 10 mL injectable liquid pharmaceutical formulation of epinephrine into each said at least one intravenous fluid bag or medication port thereof. The method further comprises the diluting of epinephrine to a concentration of about 1 microgram per mL in each said at least one intravenous fluid bag during said continuous intravenous infusion of epinephrine. The method optionally comprises protecting the at least one said intravenous fluid bag from light or UV-radiation after the step of injecting the prefilled syringe into the at least one intravenous fluid bag or medication port thereof to prevent epinephrine degradation and impurities from forming. The at least one intravenous fluid bag after injecting with the epinephrine prefilled syringe, and or the continuous intravenous infusion of epinephrine, have a ratio of 1-epinehrine:d-epinephrine greater than 4:1 and preferably at least 9:1.

Other variations and embodiments of the invention described herein will now be apparent to those of skill in the art without departing from the disclosure of the invention or the coverage of the claims to follow.

What is claimed is:

1. A method of treating a cardiac arrhythmia in a patient having or recovering from invasive orthopedic or gynecological procedures, surgery, or a combination thereof, the method comprising:
    injecting said patient with an at least 1 microgram per mL solution of l-epinephrine in saline into a subarachnoid space, epidural space, or a combination thereof to prolong anesthesia; and
    then administering a continuous intravenous infusion of l-epinephrine via an at least one intravenous fluid bag with either or both of an at least one intravenous line and an at least one intravenous catheter,
    wherein at least one syringe of a 1 mg injectable liquid pharmaceutical formulation of 1-epinephrine is injected into each said at least one intravenous fluid bag or medication port thereof, thereby diluting the formulation of 1-epinephrine to a concentration of about 1 microgram per mL during said continuous intravenous infusion of 1-epinephrine, said at least one syringe of a 1 mg injectable liquid pharmaceutical formulation of 1-epinephrine including a tonicity agent and having no more than 12.5% total impurities or no more than 12% d-epinephrine, and
    wherein said at least one intravenous fluid bag comprises, prior to injection of the at least one syringe of a 1 mg injectable liquid pharmaceutical formulation of 1-epinephrine, up to about 1,000 mL of a dextrose-containing solution, a saline-containing solution, or a combination thereof.

2. A method of treating hypotension in a patient having or recovering from invasive orthopedic or gynecological procedures, surgery, or a combination thereof, the method comprising:
    injecting an at least one syringe of a 1 mg injectable liquid pharmaceutical formulation of 1-epinephrine into an at least one intravenous fluid bag or medication port thereof, said at least one syringe of a 1 mg injectable liquid pharmaceutical formulation of 1-epinephrine including a tonicity agent and having no more than 12.5% total impurities or no more than 12% d-epinephrine;
    injecting said patient with an at least 1 microgram per mL of 1-epinephrine in anesthetic solution into a subarachnoid space to treat or prevent pain; and
    administering a continuous intravenous infusion of l-epinephrine via the at least one injected intravenous fluid bag with an at least one intravenous line, an at least one intravenous catheter, or a combination thereof,
    wherein said at least one intravenous fluid bag comprises, prior to injection of the at least one syringe of a 1 mg injectable liquid pharmaceutical formulation of 1-epinephrine, up to about 1,000 mL of a dextrose-containing solution, a saline-containing solution, or a combination thereof, and
    wherein said 1-epinephrine is diluted to a concentration of about 1 microgram per mL in each said at least one said intravenous fluid bag during said continuous intravenous infusion of 1-epinephrine.

3. A method of treating a cardiac arrhythmia or hypotension in a patient having or recovering from invasive orthopedic or gynecological procedures, surgery, or a combination thereof, said method comprising:
    replacing general anesthesia with regional anesthesia;
    injecting said patient with an at least 1 microgram per mL of 1-epinephrine in anesthetic solution into a subarachnoid space, epidural space, or a combination thereof to treat pain, wherein said at least 1 microgram per mL of 1-epinephrine in anesthetic solution is prepared, just prior to said injecting into said subarachnoid space, epidural space, or a combination thereof, by mixing at least some of a 1 mg injectable liquid pharmaceutical formulation of 1-epinephrine including a tonicity agent and having no more than 12.5% total impurities or no more than 12% d-epinephrine with at least some of an anesthetic solution;
    injecting an at least one syringe of a 1 mg injectable liquid pharmaceutical formulation of 1-epinephrine into an at least one intravenous fluid bag or medication port thereof, said at least one syringe of a 1 mg injectable liquid pharmaceutical formulation of 1-epinephrine including a tonicity agent and having no more than 12.5% total impurities or no more than 12% d-epinephrine, and said at least one intravenous fluid bag comprising, prior to injecting the at least one syringe of the 1 mg injectable liquid pharmaceutical formulation of 1-epinephrine, up to about 1,000 mL of a dextrose-containing solution, a saline-containing solution, or a combination thereof;

providing said patient with a continuous intravenous infusion of said at least one intravenous fluid bag into which said 1 mg injectable liquid pharmaceutical formulation of 1-epinephrine has been injected, wherein said 1-epinephrine is diluted to a concentration of about 1 microgram per mL in each said at least one said intravenous fluid bag during said continuous intravenous infusion.

4. The method of claim 1, comprising protecting said at least one intravenous fluid bag from light or UV-radiation after injecting said syringe into said at least one intravenous fluid bag or medication port thereof to reduce 1-epinephrine degradation and impurities from forming.

5. The method of claim 2, comprising protecting said at least one intravenous fluid bag from light or UV-radiation after injecting said syringe into said at least one intravenous fluid bag or medication port thereof to reduce 1-epinephrine degradation and impurities from forming.

6. The method of claim 3, comprising protecting said at least one said intravenous fluid bag from light or UV-radiation after injecting said syringe into said at least one intravenous fluid bag or medication port thereof to reduce 1-epinephrine degradation and impurities from forming.

7. The method of claim 3, wherein said continuous intravenous infusion of 1-epinephrine has a ratio of 1-epinephrine:d-epinephrine greater than 4:1.

\* \* \* \* \*